(12) United States Patent
Kemp et al.

(10) Patent No.: US 11,160,927 B2
(45) Date of Patent: Nov. 2, 2021

(54) DRUG DELIVERY DEVICE

(71) Applicant: SANOFI-AVENTIS DEUTSCHLAND GMBH, Frankfurt am Main (DE)

(72) Inventors: Thomas Mark Kemp, Ashwell (GB); Hugo Revellat, Royston (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 635 days.

(21) Appl. No.: 15/578,854

(22) PCT Filed: Jun. 2, 2016

(86) PCT No.: PCT/EP2016/062456
§ 371 (c)(1),
(2) Date: Dec. 1, 2017

(87) PCT Pub. No.: WO2016/193350
PCT Pub. Date: Dec. 8, 2016

(65) Prior Publication Data
US 2018/0214637 A1    Aug. 2, 2018

(30) Foreign Application Priority Data
Jun. 3, 2015 (EP) .................................... 15170593

(51) Int. Cl.
*A61M 5/20* (2006.01)
*A61M 5/315* (2006.01)

(52) U.S. Cl.
CPC ........ *A61M 5/2033* (2013.01); *A61M 5/3158* (2013.01); *A61M 5/31578* (2013.01); *A61M 2205/581* (2013.01); *A61M 2205/582* (2013.01)

(58) Field of Classification Search
CPC .............. A61M 5/2033; A61M 5/3157; A61M 5/31578; A61M 5/3158;
(Continued)

(56) References Cited

U.S. PATENT DOCUMENTS

| | | | |
|---|---|---|---|
| 2013/0035642 A1* | 2/2013 | Daniel | A61M 5/3158 604/189 |
| 2013/0296796 A1* | 11/2013 | Hourmand | A61M 5/326 604/197 |

(Continued)

FOREIGN PATENT DOCUMENTS

| | | |
|---|---|---|
| CN | 103476443 | 12/2013 |
| CN | 103492000 | 1/2014 |

(Continued)

OTHER PUBLICATIONS

International Search Report and Written Opinion in International Application No. PCT/EP2016/062456, dated Aug. 17, 2016, 8 pages.

(Continued)

*Primary Examiner* — Bradley J Osinski
(74) *Attorney, Agent, or Firm* — Fish & Richardson P.C.

(57) ABSTRACT

The present disclosure relates to a drug delivery device having a case adapted to retain a medicament container, a plunger disposed within the case and slidable from a proximal position into a distal position for delivering a medicament from the medicament container, and at least one feedback mechanism that is in operative connection with the plunger. The feedback mechanism includes a collar, a needle shroud, and a control spring biasing the needle shroud in a distal direction relative to the collar. The collar is operatively coupled to the case in an axial direction and prevented from axially decoupling from the case by the plunger when in the proximal position. The plunger, during movement from the proximal position towards the distal position, allows axial decoupling of the collar from the case driven by the control spring until the collar's movement is halted, which creates an audible and/or tactile feedback.

18 Claims, 27 Drawing Sheets

(58) Field of Classification Search
CPC .... A61M 2005/2013; A61M 2005/208; A61M 2205/581; A61M 2205/582
See application file for complete search history.

(56) References Cited

U.S. PATENT DOCUMENTS

2013/0310744 A1* 11/2013 Brereton ............ A61M 5/2033
604/111
2016/0008542 A1 1/2016 Hirschel et al.

FOREIGN PATENT DOCUMENTS

| | | |
|---|---|---|
| CN | 104023769 | 9/2014 |
| EP | 2468335 | 6/2012 |
| EP | 2489383 | 8/2012 |
| EP | 2823841 | 1/2015 |
| WO | WO 2012/110572 | 8/2012 |
| WO | WO 2012/110576 | 8/2012 |
| WO | WO 2013/057032 | 4/2013 |
| WO | WO 2014/146209 | 9/2014 |

OTHER PUBLICATIONS

International Preliminary Report on Patentability in International Application No. PCT/EP2016/062456, dated Dec. 5, 2017, 6 pages.

* cited by examiner

DRUG DELIVERY DEVICE

CROSS REFERENCE TO RELATED APPLICATIONS

The present application is the national stage entry of International Patent Application No. PCT/EP2016/062456, filed on Jun. 2, 2016, and claims priority to Application No. EP 15170593.6, filed in on Jun. 3, 2015, the disclosures of which are expressly incorporated herein in entirety by reference thereto.

TECHNICAL FIELD

The disclosure generally relates to a drug delivery device.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by a plunger which is continuously pressed during the injection. There are numerous disadvantages associated with this approach. For example, if the plunger is released prematurely, the injection will stop and may not deliver an intended dose. Furthermore, the force required to push the plunger may be too high (e.g., if the user is elderly or a child). And, aligning the injection device, administering the injection, and keeping the injection device still during the injection may require dexterity which some patients may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Furthermore, it is desirable to administer the full dose in order to achieve full effectiveness of the medicament within the patient.

Thus, there remains a need for an improved drug delivery device.

SUMMARY

Certain aspects of the disclosure relate to an improved drug delivery device.

According to the present disclosure, a drug delivery device comprises:
 a case adapted to retain a medicament container,
 a plunger disposed within the case and slidable from a proximal position into a distal position for delivering a medicament from the medicament container,
 at least one feedback mechanism that is in operative connection with the plunger, the feedback mechanism comprising a collar, a needle shroud, a control spring biasing the needle shroud in a distal direction relative to the collar, the collar operatively coupling to the case in an axial direction and prevented from axially decoupling from the case by the plunger when in the proximal position, wherein the plunger, during movement from the proximal position towards the distal position, is adapted to allow axial decoupling of the collar from the case driven by the control spring until the collar's movement is halted to create an audible and/or tactile feedback.

In an exemplary embodiment, the collar is adapted to abut the case to create the audible and/or tactile feedback The drug delivery device is improved due to the feedback mechanism used for indicating to a patient or user that the full dose of medicament was spent.

In an exemplary embodiment, the collar comprises one or more resilient joints, e.g. snap-fit joints, adapted to axially interact with the case, the joints biased inward, wherein the plunger in the proximal position is adapted to inwardly support the joints to prevent their inward movement and wherein the plunger in the distal position is axially removed from the joints, allowing their inward movement, and thus allowing decoupling of the joints from the case.

In an exemplary embodiment, the control spring is arranged as a compression spring.

In an exemplary embodiment, the drug delivery device further comprises a plunger release mechanism adapted for preventing release of the plunger when the needle shroud is in a distal position and adapted to release the plunger when the needle shroud is in a proximal position.

In an exemplary embodiment, the plunger release mechanism comprises a cam surface on the collar and a boss on the plunger adapted to engage the cam surface so that a distally directed force applied to the plunger causes the boss to abut the cam surface to bias the collar in a rotational direction.

In an exemplary embodiment, the plunger boss is guided in a longitudinal slot within the case.

In an exemplary embodiment, the slot is wider than the plunger boss, allowing rotational movement of the plunger boss and plunger relative to the case.

In an exemplary embodiment, a shroud boss is arranged on the needle shroud and adapted to contact a first collar rib on the collar during assembly of the drug delivery device, wherein the shroud boss and/or the first collar rib are/is angled so that proximal motion of the needle shroud causes the collar to rotate in a rotational direction.

In an exemplary embodiment, the cam surface comprises two ramps defining a tip, wherein the collar's rotation in the rotational direction due to proximal motion of the needle shroud during assembly of the drug delivery device causes the plunger boss to move past the tip of the cam surface.

In an exemplary embodiment, an L-shaped second collar rib is provided on the collar, adapted to laterally abut the shroud boss to prevent further rotation of the collar and to maintain the coupling of the cam surface to the plunger boss when the needle shroud is in a distal position, wherein the shroud boss disengages the second collar rib when the needle shroud is in a proximal position, allowing further rotation of the collar to decouple the plunger boss from the cam surface to release the plunger.

In an exemplary embodiment, an interface on the collar is adapted to engage a case rib on the case, wherein the interface comprises two lateral surfaces adapted to operatively abut the case rib allowing rotation of the collar relative to the case.

In an exemplary embodiment, the interface comprises a distal surface adapted to abut the case rib, preventing movement of the collar in the distal direction relative to the case.

In an exemplary embodiment, a ramped surface, e.g. arranged on the case, is adapted to abut the collar as the collar moves after release of the feedback mechanism, the abutment of the ramped surface imparting a torque on the collar for aligning the second collar rib in an axial path of the shroud boss after extension of the needle shroud from the proximal position to the distal position.

In an exemplary embodiment, an angular stop, e.g. arranged in the case, is adapted to abut the collar and prevent rotation of the collar beyond alignment of the second collar rib in the axial path of the shroud boss.

In an exemplary embodiment, the case comprises a front case and a rear case adapted to be coupled to each other.

Exemplary embodiments are provided in the dependent claims.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
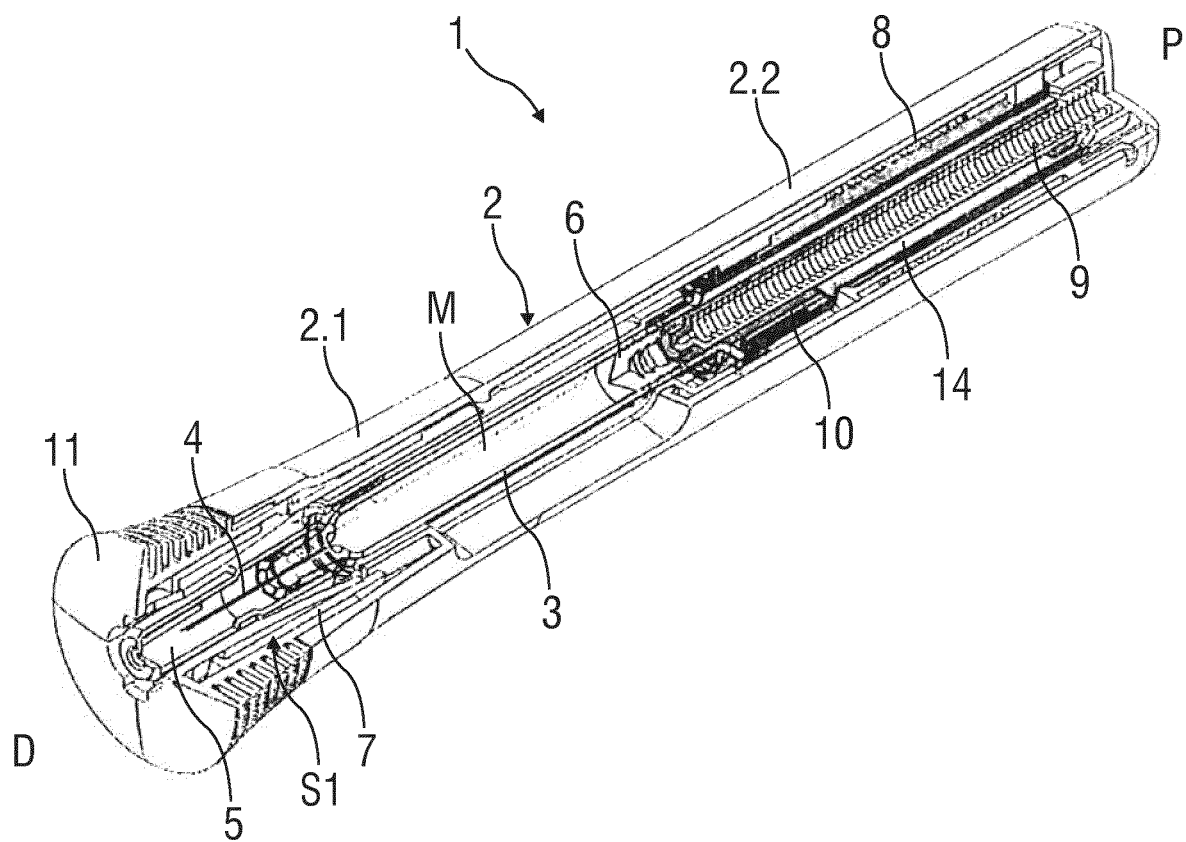
FIG. 1 is a perspective view of an exemplary embodiment of an auto-injector.

FIG. 1 is a perspective view of an exemplary embodiment of an auto-injector 1. The auto-injector 1 comprises a case 2 comprising a sleeve-shaped front case 2.1 and a rear case 2.2. A cap 11 is attached at a distal end of the case 2. A sleeve-shaped needle shroud 7 is telescoped within the case 2. The case 2 is adapted to receive a medicament container 3, such as a syringe 3, for example a glass syringe. The medicament container 3 is referred to hereinafter as the "syringe 3". The syringe 3 may be a pre-filled syringe containing a medicament M and having a needle 4 arranged at a distal end of the syringe 3. In another exemplary embodiment, the medicament container 3 may be a cartridge which includes the medicament M and engages a removable needle (e.g., by threads, snaps, friction, etc.) When the auto-injector 1 or the syringe 3 is assembled, a protective needle sheath 5 is attached to the needle 4. A stopper 6 is arranged for sealing the syringe 3 proximally and for displacing a liquid medicament M contained in the syringe 3 through the hollow needle 4. The syringe 3 is held in the case 2 and supported at its proximal end therein.

The protective needle sheath 5 may be coupled to the cap 11 so that when the cap 11 is removed, the protective needle sheath 5 is also removed from the needle 4. The cap 11 may comprise grip features 11.5 for facilitating removal of the cap 11.

The sleeve-shaped needle shroud 7 is telescoped in the distal end of the case 2. A control spring 8 is arranged to bias the needle shroud 7 in a distal direction D against the case 2.

A drive spring 9 in the shape of a compression spring is arranged within a proximal part of the case 2. A plunger 10 serves for forwarding the force of the drive spring 9 to the stopper 6. In an exemplary embodiment, the plunger 10 is hollow and the drive spring 9 is arranged within the plunger 10, biasing the plunger 10 in the distal direction D against the rear case 2.2.

The auto-injector 1 may be divided in two subassemblies, a control subassembly 1.1 and a drive subassembly 1.2. This allows for improving flexibility as to the time and location of manufacture of the subassemblies 1.1, 1.2 and final assembly with the syringe 3.

Figure 2:
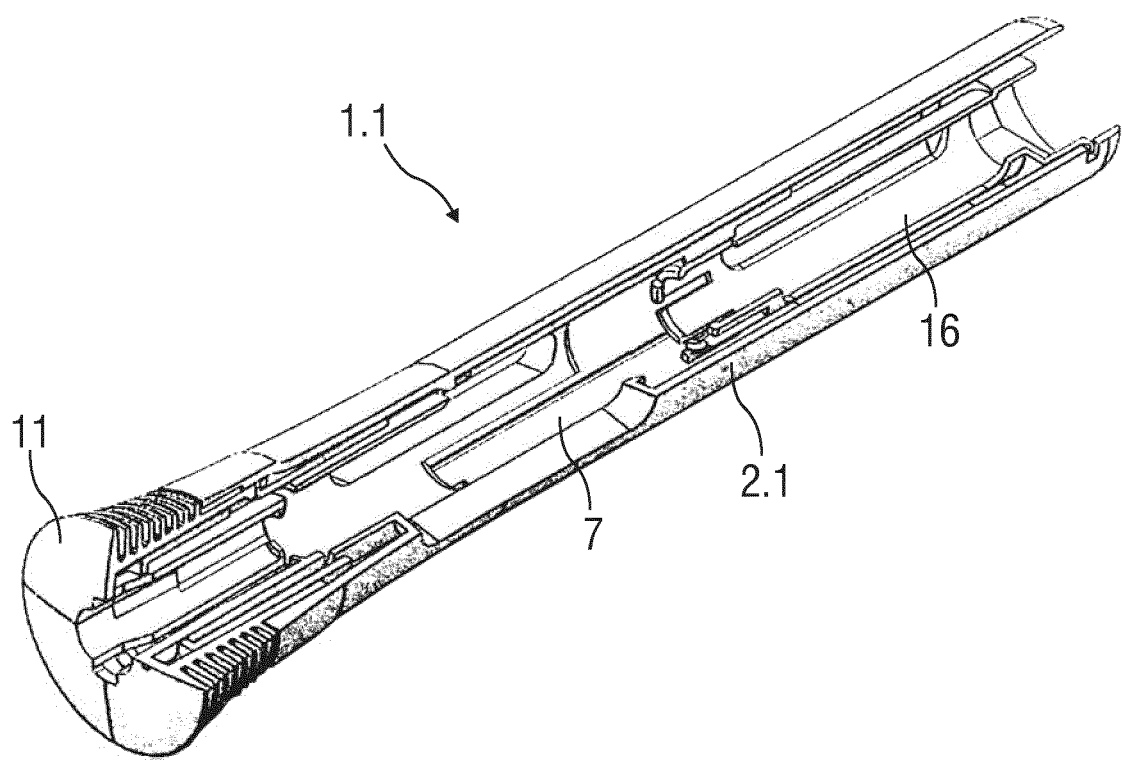
FIG. 2 is a perspective view of a control subassembly.
Figure 3:
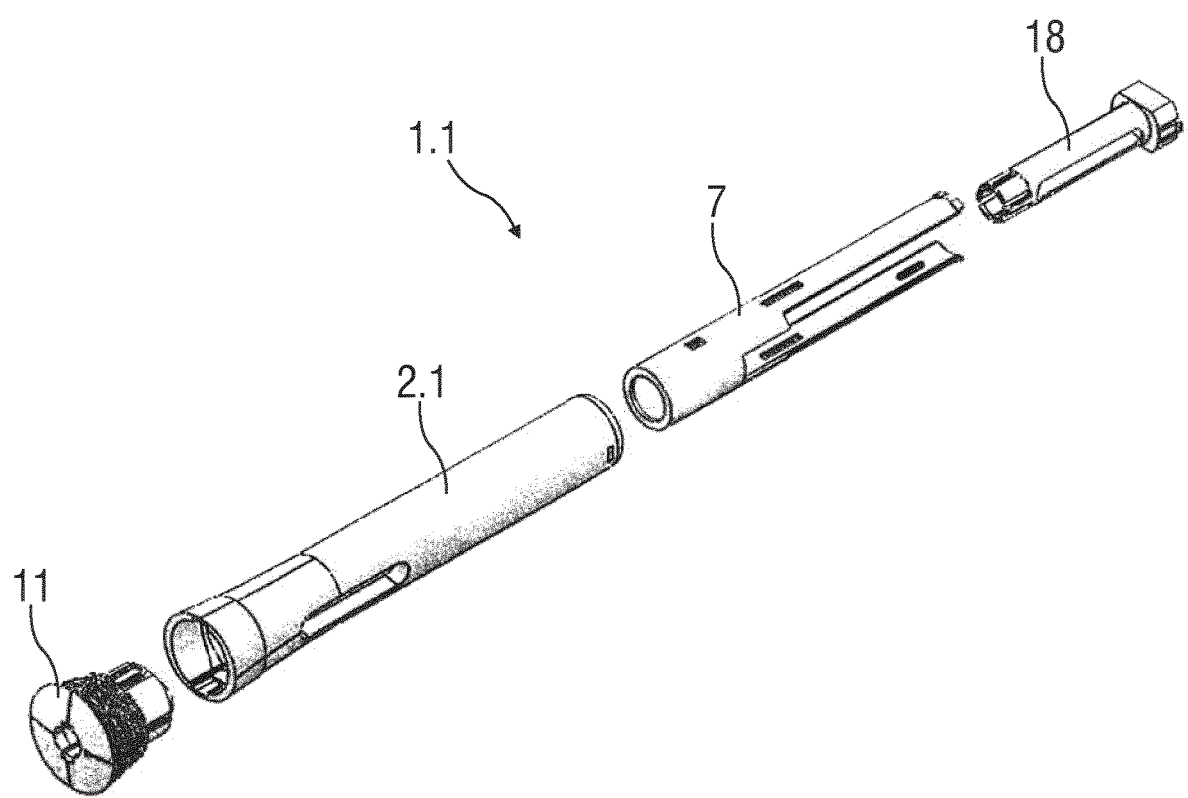
FIG. 3 is a perspective exploded view of the control subassembly.

FIG. 2 is a perspective view of the control subassembly 1.1. FIG. 3 is a perspective exploded view of the control subassembly 1.1. The control subassembly 1.1 comprises all parts and mechanisms which control access to the needle 4 and the forces a user will feel when they use the auto-injector 1. The control subassembly 1.1 comprises the cap 11, the needle shroud 7 and the front case 2.1. In an exemplary embodiment, the control mechanism 1.1 may additionally comprise a sleeve shaped carrier 18 for retaining the syringe 3. In other embodiments, the syringe 3 may be directly received within the front case 2.1.

Figure 4:
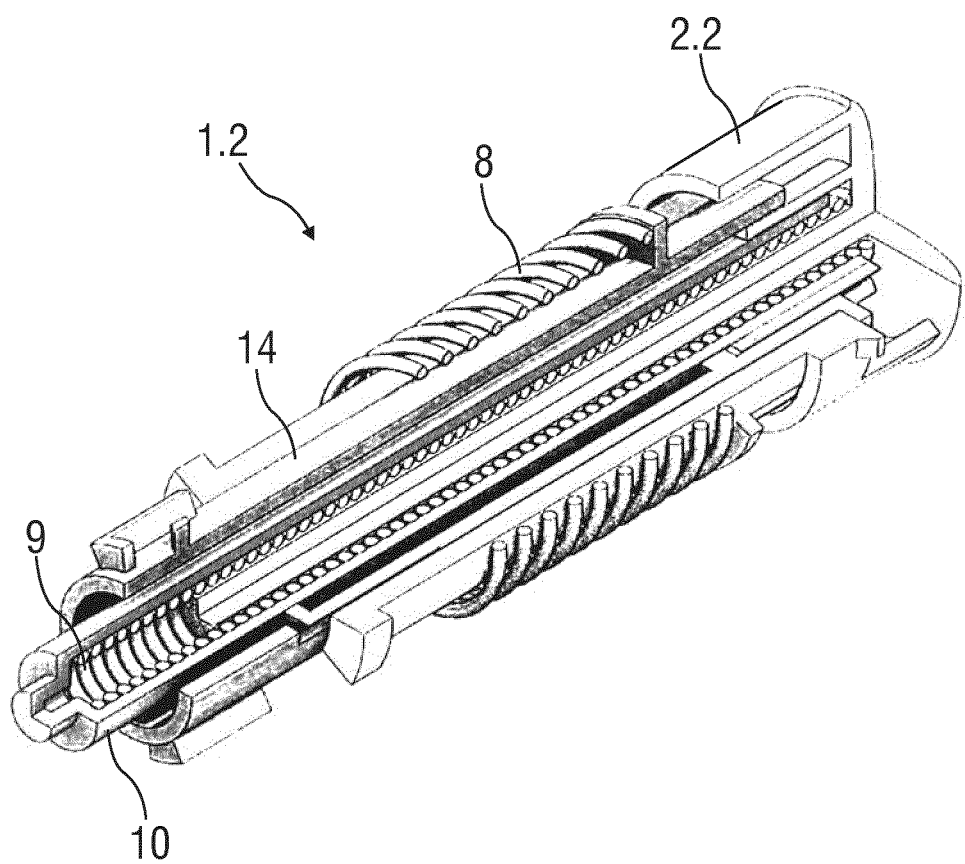
FIG. 4 is a perspective view of a drive subassembly.
Figure 5:
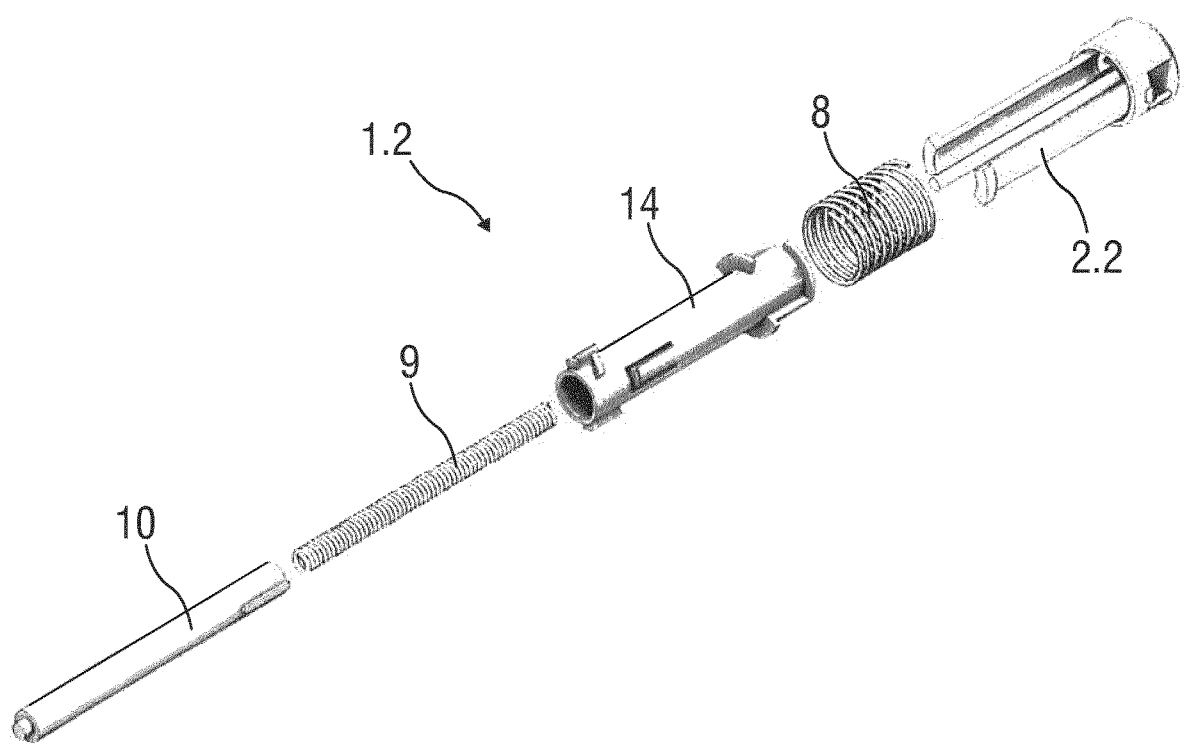
FIG. 5 is a perspective exploded view of the drive subassembly.

FIG. 4 is a perspective view of the drive subassembly 1.2. FIG. 5 is a perspective exploded view of the drive subassembly 1.2. The drive subassembly 1.2 comprises the components required to deliver the medicament M. If the viscosity or volume of the medicament M in the syringe 3 is varied, only parts of the drive subassembly 1.2 may need to be changed. The drive subassembly 1.2 comprises the plunger 10, the drive spring 9, the rear case 2.2, the control spring 8 and a sleeve shaped collar 14 which will be explained in more detail below.

Figure 6:
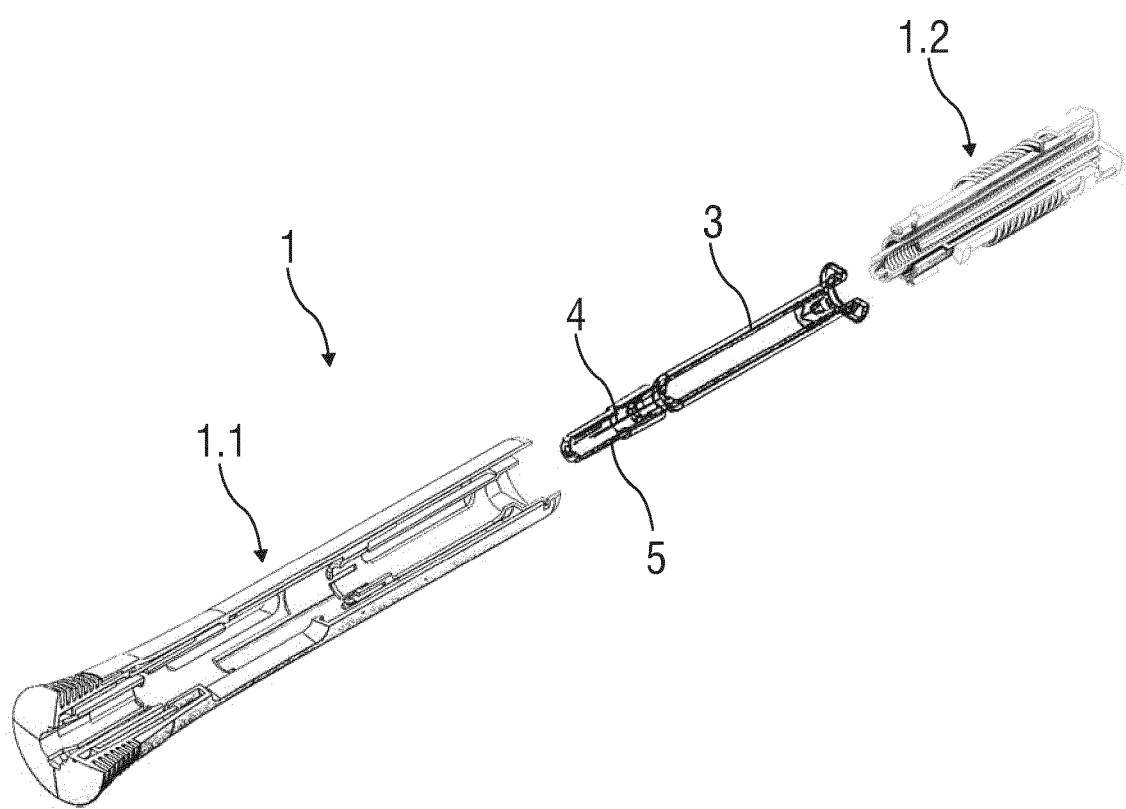
FIG. 6 is a schematic exploded view of the auto-injector during assembly.

FIG. 6 is a schematic exploded view of the auto-injector 1 during assembly. In order to assemble the auto-injector 1, a syringe 3 with an attached needle 4 and a protective needle sheath 5 is inserted into the control subassembly 1.1 in the distal direction D. Afterwards, the drive subassembly 1.2 is inserted into the control subassembly 1.1 in the distal direction D.

Figure 7:
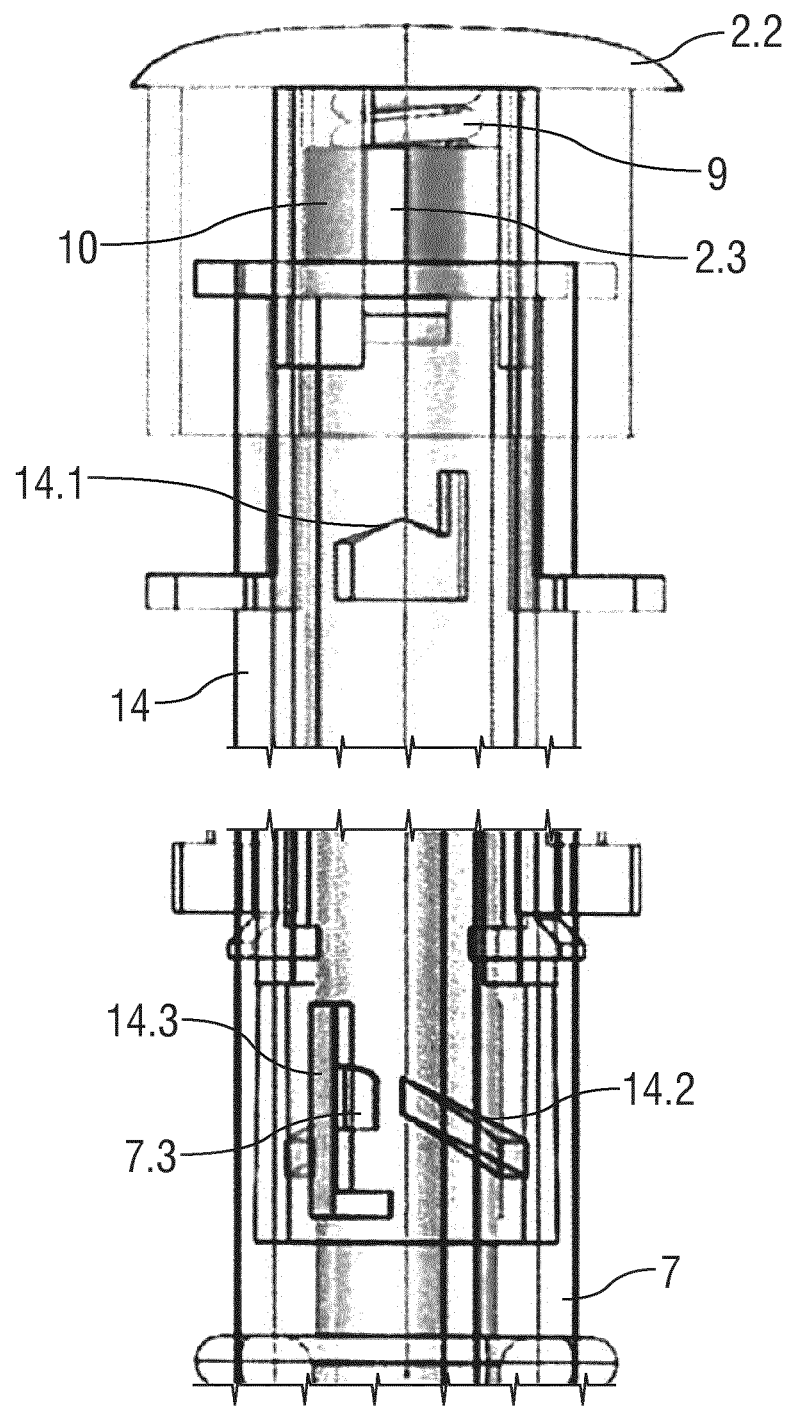
FIG. 7 is a semi-transparent schematic detail side view of the auto-injector showing a plunger release mechanism.

FIG. 7 is a semi-transparent schematic detail side view of the auto-injector 1 showing a plunger release mechanism 12. The plunger release mechanism 12 is arranged for preventing release of the plunger 10 prior to depression of the needle shroud 7 and for releasing the plunger 10 once the needle shroud 7 is sufficiently depressed.

The plunger release mechanism 12 is adapted to control the automated activation of syringe emptying. The plunger release mechanism 12 is activated immediately prior to full needle insertion. The plunger release mechanism 12 comprises the plunger 10, the rear case 2.2, the collar 14 and the needle shroud 7. The needle shroud 7 is operationally coupled to the collar 14 and adapted to push the collar 14 in a proximal direction P.

The needle shroud 7, the rear case 2.2 and the collar 14 are configured to move only in an axial direction, i.e. in the distal direction D and the proximal direction P, whereas the plunger 10 can both move rotationally in rotational directions R1, R2 and axially in the distal direction D and the proximal direction P. In an exemplary embodiment, there may be no compliant part in the plunger release mechanism 12, i.e. the parts may be all rigid and move as a whole with no relative deformation within a part. The plunger release mechanism 12 is schematically illustrated in five different states in FIGS. 8A to 8E.

Figure 8A:
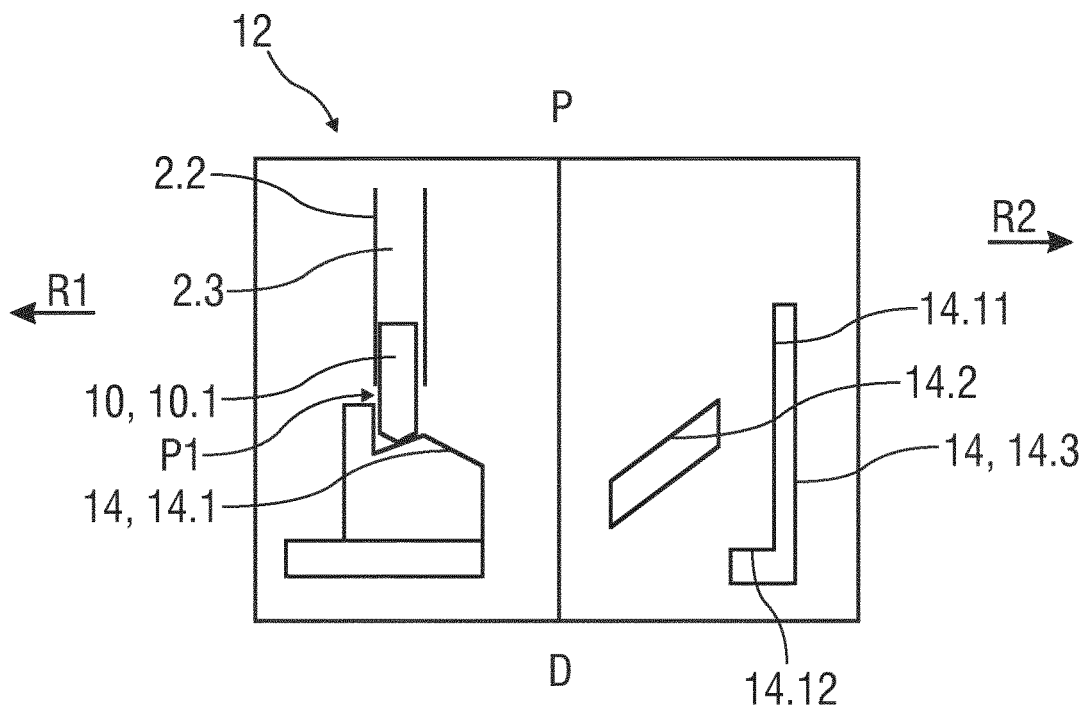
FIG. 8A is a schematic view of a plunger release mechanism in a pre-assembly or pre-use state.

FIG. 8A shows the plunger release mechanism 12 in a pre-assembly state with the plunger 10 in a proximal position P1. In the pre-assembly state, a boss 10.1 on the plunger 10 is sited on a roof-shaped cam surface 14.1, e.g. an extruded path, within the collar 14, which prevents the plunger 10 from moving in the distal direction D when a force in the distal direction D is applied to the plunger 10, e.g. by the drive spring 9. The cam surface 14.1 is angled to induce a small torque forcing the plunger 10 to rotate in a first rotational direction R1 and the collar 14 to slightly rotate in the opposite second rotational direction R2. The rotation of the plunger 10 in the first rotational direction R1 is stopped by the plunger boss 10.1 being engaged in a longitudinal slot 2.3 in the rear case 2.2. The slot 2.3 is slightly wider than the plunger boss 10.1, allowing for a limited rotational movement of the plunger boss 10.1 and plunger 10.

Figure 8B:
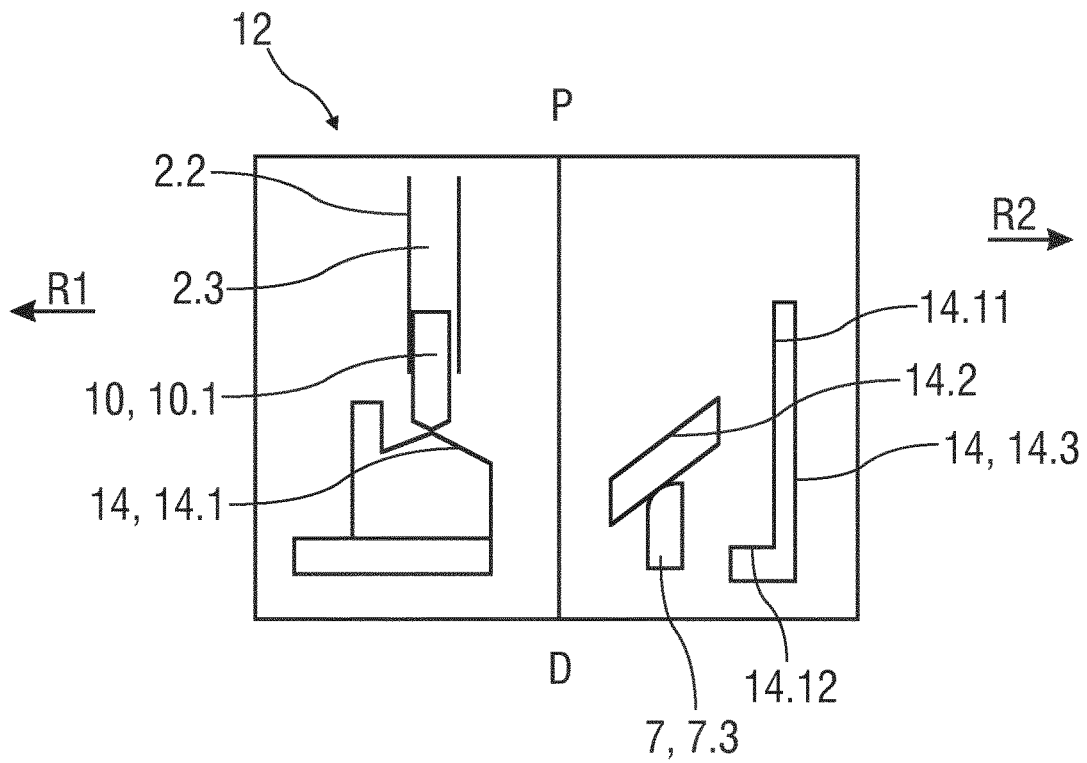
FIG. 8B is a schematic view of the plunger release mechanism during assembly.

FIG. 8B shows the plunger release mechanism 12 in a state during insertion of the drive sub-assembly 1.2 into the control sub-assembly 1.1. A shroud boss 7.3 on the needle shroud 7 comes into contact with a first collar rib 14.2 on the collar 14. The shroud boss 7.3 and the first collar rib 14.2 are designed so that the proximal motion of the needle shroud 7 causes the collar 14 to slightly rotate in the first rotational direction R1. This sets the plunger boss 10.1 in an unstable position on a tip of the cam surface 14.1. In the illustrated embodiment, the first collar rib 14.2 is angled to achieve this. In other embodiments, the shroud boss 7.3 may be angled instead of the first collar rib 14.2. Likewise, both the first collar rib 14.2 and the shroud boss 7.3 may be angled.

Figure 8C:
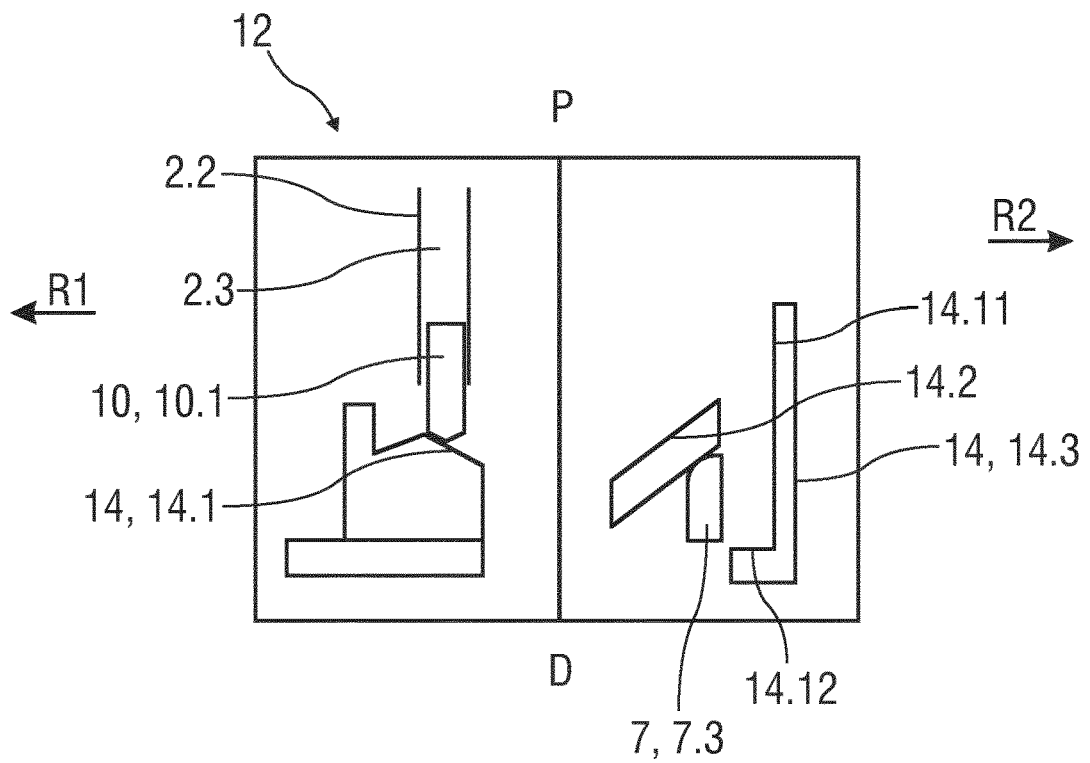
FIG. 8C is a schematic view of the plunger release mechanism during assembly.

FIG. 8C shows the plunger release mechanism 12 in a state during further insertion of the drive sub-assembly 1.2 into the control sub-assembly 1.1. Due to its unstable position, a rotational motion of the plunger 10 in the second rotational direction R2 is initiated and stops almost immediately due to the width of the slot 2.3 in the rear case 2.2, in which the boss 10.1 is guided. The collar 14 keeps rotating in the first rotational direction R1 under the action of the needle shroud 7. In addition, the plunger 10, driven by the drive spring 9, now fosters the rotation of the collar 14 as well, as the plunger boss 10.1 starts to fall along the cam surface 14.1 on the collar 14.

Figure 8D:
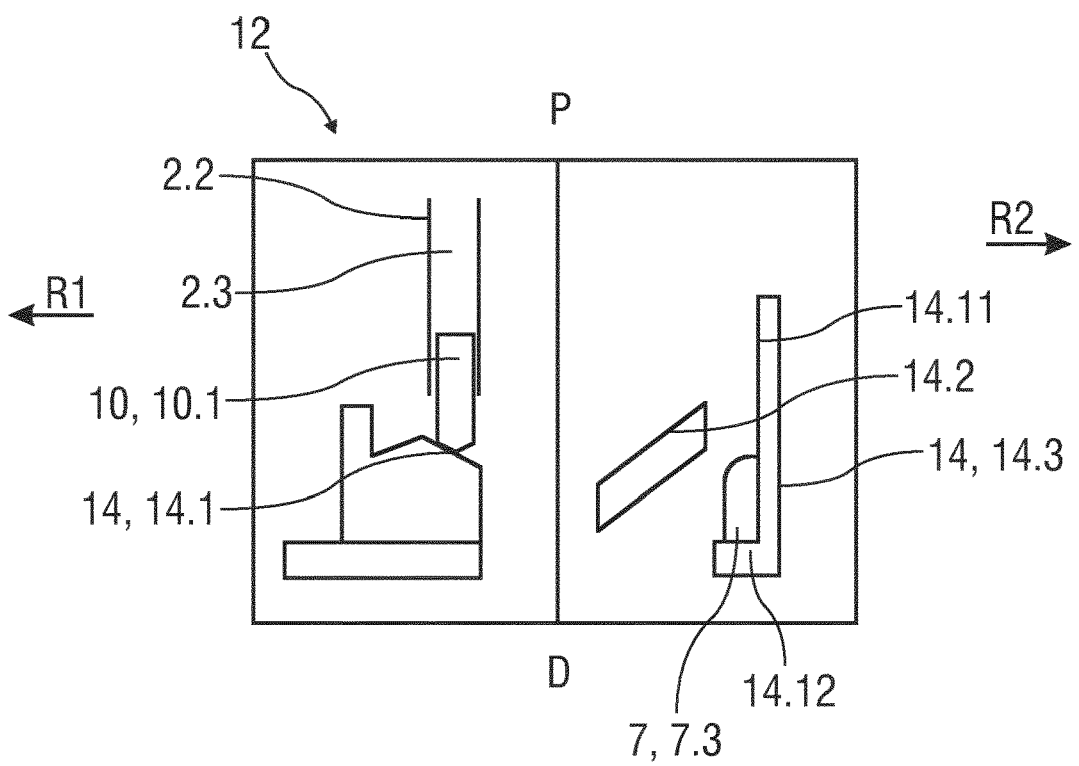
FIG. 8D is a schematic view of the plunger release mechanism in a pre-use state.

FIG. 8D shows the plunger release mechanism 12 in a pre-use state. The rotational motion of the collar 14 in the first rotational direction R1 is stopped when the shroud boss 7.3 ends its course along the first collar rib 14.2 and laterally abuts a first longitudinal surface 14.11 of an L-shaped second collar rib 14.3. As the plunger boss 10.1 still sits on the cam surface 14.1 of the collar 14, the plunger 10 is prevented from being released. The shroud boss 7.3 engages proximally behind a transversal surface 14.12 of the L-shaped second collar rib 14.3 preventing subsequent movement of the needle shroud 7 in the distal direction D relative to the collar 14.

The plunger release mechanism 12 is in its pre-use configuration.

Figure 8E:
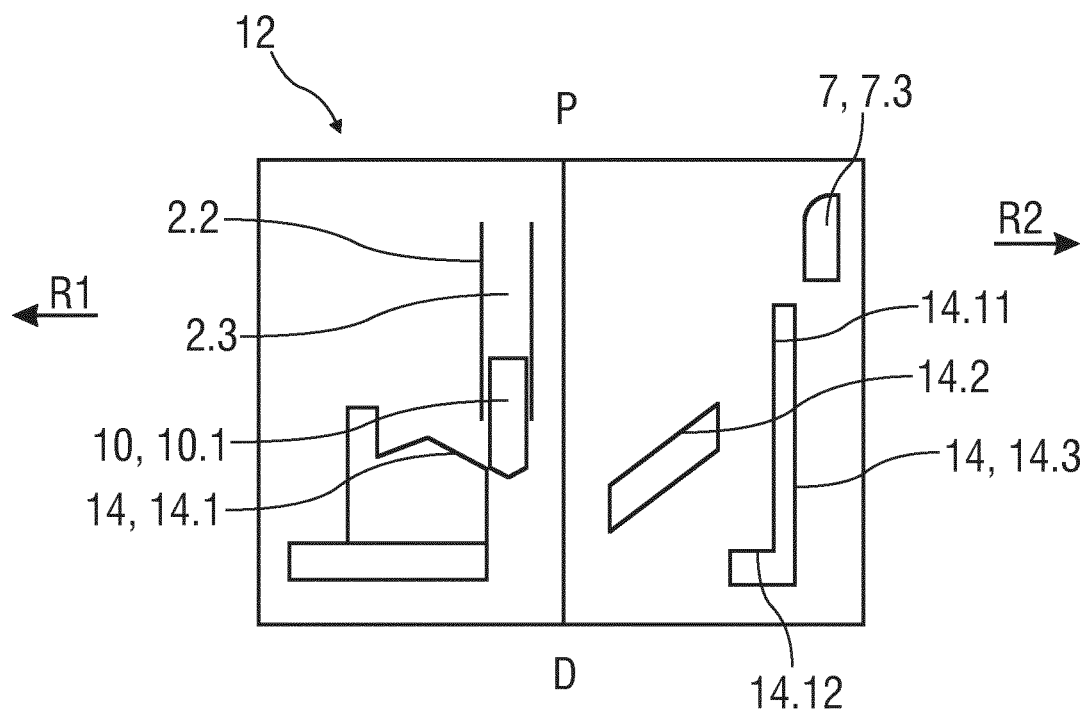
FIG. 8E is a schematic view of the plunger release mechanism during release of a plunger.

FIG. 8E shows the plunger release mechanism 12 in a state at the beginning of an injection. The needle shroud 7 is moved in the proximal direction P into the front case 2.1, e.g. by a user pressing the needle shroud 7 against an injection site, thereby inserting the needle 4 into the injection site. During this motion, the shroud boss 7.3 moves in the proximal direction P along the first longitudinal surface 14.11 of the L-shaped second collar rib 14.3. When full needle insertion depth is reached, the shroud boss 7.3 travels beyond a proximal end of the first longitudinal surface 14.11 of the second collar rib 14.3. The plunger boss 10.1, biased by the drive spring 9 in the distal direction D and acting on the cam surface 14.1 thus rotates the collar 14 in the first rotational direction R1 until the plunger boss 10.1 reaches the end of the cam surface 14.1, allowing the plunger 10 to move in the distal direction D without being further subjected to torque. Under the action of the drive spring 9, the plunger 10 pushes on the stopper 6 and starts to empty the content of the syringe 3.

Figure 9A:
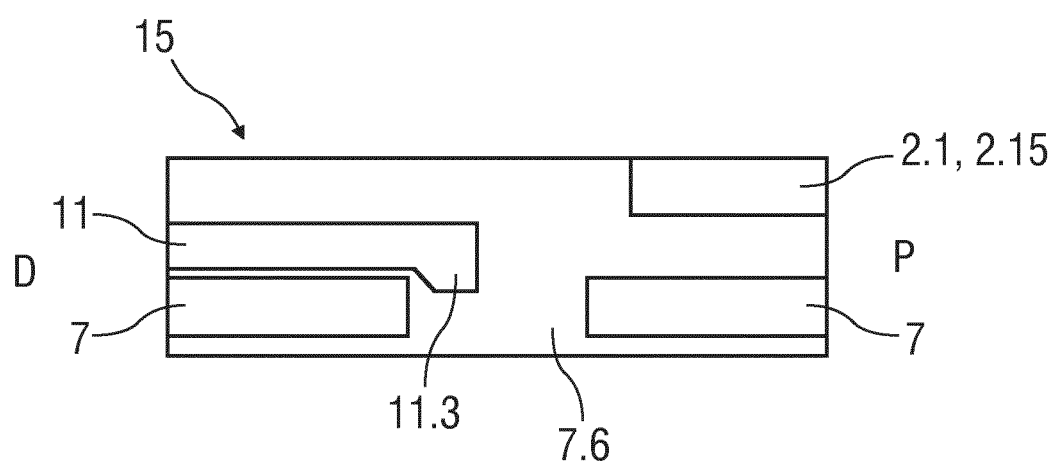
FIG. 9A is a schematic view of a first shroud lock mechanism.

FIG. 9A is a schematic view of a first shroud lock mechanism 15. The first shroud lock mechanism 15 is arranged to prevent depression of the needle shroud 7 when the cap 11 is in place, thus avoiding unintentional activation of the auto-injector 1 upon drop. The first shroud lock mechanism 15 comprises one, two or more compliant beams 11.3 on the cap 11 and a respective number of apertures 7.6 in the needle shroud 7, in which the compliant beams 11.3 may engage. The compliant beams 11.3 and/or the apertures 7.6 are ramped so as to radially outwardly deflect the compliant beams 11.3 out of the apertures 7.6 on movement of the cap 11 in the distal direction D relative the needle shroud 7. Depending on an axial position of the cap 11 engaged to the shroud 7 relative the case 2, a radial stop 2.15 on the case 2 prevents or allows radially outward deflection of the compliant beams 11.3, thus preventing the needle shroud 7 from disengaging the cap 11 and constraining depression of the needle shroud 7 in the proximal direction P relative the case 2. Axial movement of the cap 11 in the proximal direction P relative the case 2 may be limited by a rib on the cap 11 abutting the case 2.

Figure 9B:
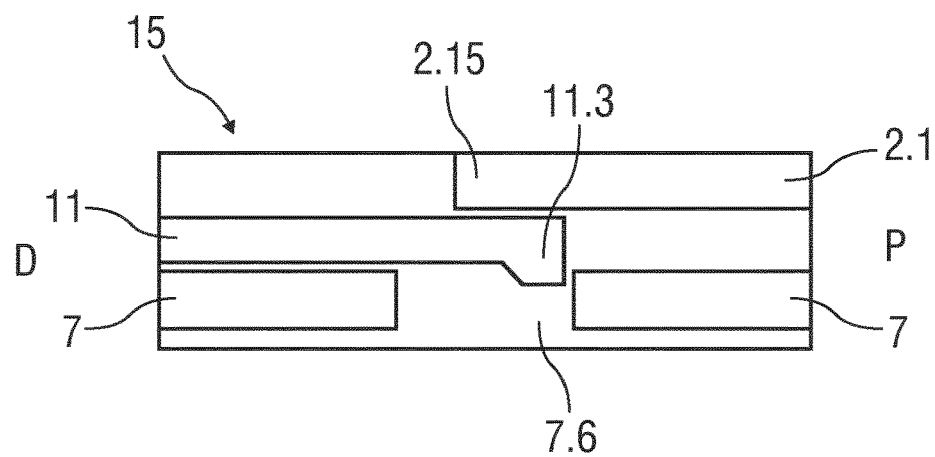
FIG. 9B is a schematic view of a first shroud lock mechanism.
Figure 9C:
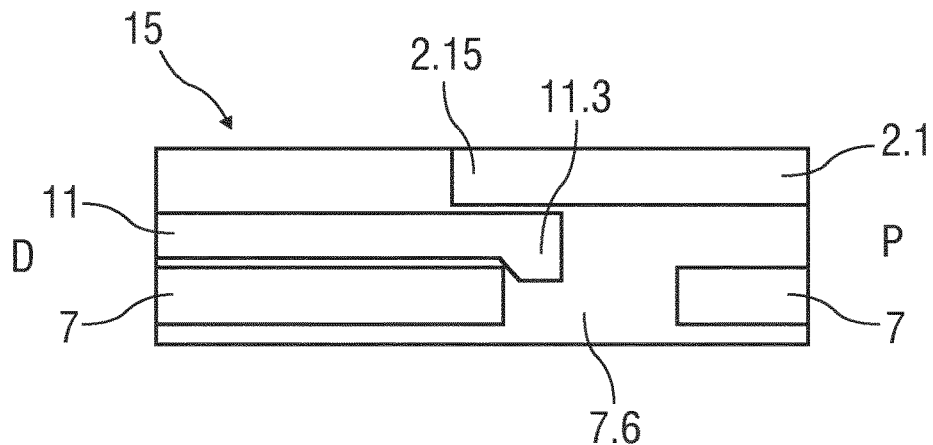
FIG. 9C is a schematic view of a first shroud lock mechanism.

FIG. 9A is a schematic view of the first shroud lock mechanism 15 after assembly of the control subassembly 1.1. The compliant beam 11.3 on the cap 11 is engaged in the aperture 7.6 within the needle shroud 7. The radial stop 2.15 is axially spaced from the compliant beam 11.3. FIG. 9B is a schematic view of the first shroud lock mechanism 15 during insertion of the syringe 3 into the control subassembly 1.1 for engaging the protective needle sheath 5 to the cap 11. The aperture 7.6 provides some clearance allowing a movement of the needle shroud 7 relative the cap 11 in the distal direction D. The front case 2.1 is also moved in the distal direction D relative the cap 11 axially aligning the radial stop 2.15 with the compliant beam 11.3, preventing the cap 11 from disengaging the needle shroud 7. FIG. 9C is a schematic view of the first shroud lock mechanism 15, wherein after insertion of the syringe 3, the needle shroud 7 is moved further in the proximal direction P relative the front case 2.1, e.g. by an assembly jig (not illustrated). In this state, the drive subassembly 1.2 may be assembled to the control subassembly 1.1. The compliant beam 11.3 remains engaged in the aperture 7.6 and the radial stop 2.15 prevents them from disengaging.

After assembly of the drive subassembly 1.2 to the control subassembly 1.1 the assembly jig is removed allowing the needle shroud 7 to move back in the distal direction D relative the front case 2.1, arriving again in the state illustrated in FIG. 9B. If the auto-injector 1 is accidentally dropped in this state, the needle shroud 7 may move in the proximal direction P relative the case 2 under inertial forces until the distal end of the aperture 7.6 in the needle shroud 7 contacts the compliant beam 11.3 as in FIG. 9C. As the compliant beam 11.3 is prevented from disengaging the aperture 7.6 by the radial stop 2.15 and due to the rib 11.4 on the cap 11 axially abutting the front case 2.1, the needle shroud 7 cannot move further in the proximal direction P, thereby avoiding unintentional triggering of the auto-injector 1.

Figure 9D:
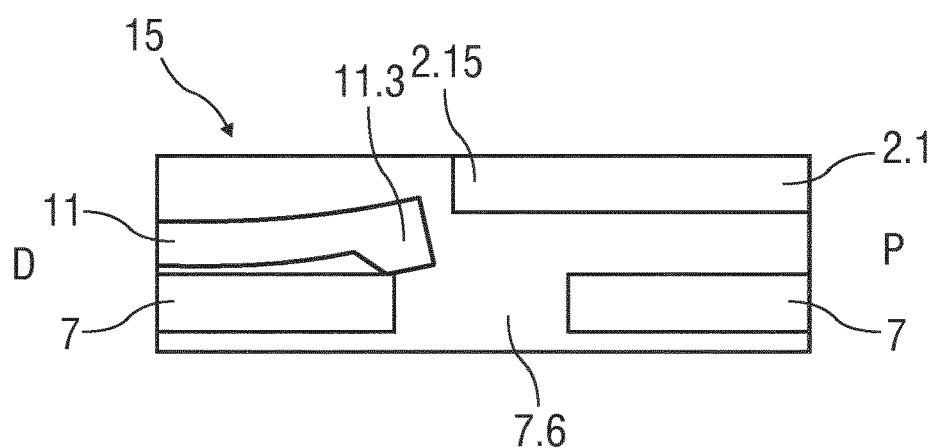
FIG. 9D is a schematic view of a first shroud lock mechanism.

FIG. 9D is a schematic view of the first shroud lock mechanism 15 during removal of the cap 11 with the compliant beam 11.3 being deflected out of the aperture 7.6 by ramped action.

A feedback mechanism 13 is arranged for enabling emission of an audible and/or tactile feedback indicating the completion of medicament delivery. The feedback mechanism 13 is schematically illustrated in six different states in FIGS. 10A to 10C.

The feedback mechanism 13 comprises the plunger 10, the rear case 2.2, the needle shroud 7, the collar 14 and the control spring 8.

Figure 10A:
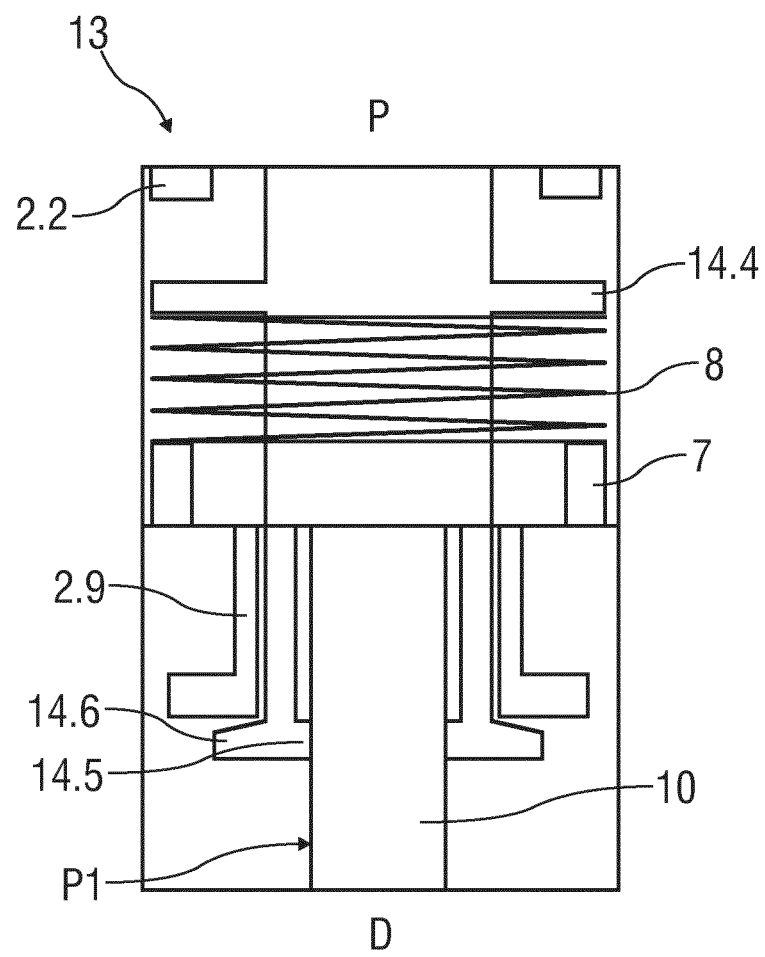
FIG. 10A is a schematic view of a feedback mechanism in the pre-use state.

FIG. 10A shows the feedback mechanism 13 in the pre-use state. The control spring 8 is compressed between two third collar ribs 14.4 on the collar 14 and the needle shroud 7. The plunger 10 is arranged within the collar 14 between inner protrusions 14.5 of joints 14.6 on the collar 14. Consequently, the joints 14.6 cannot deflect inward. The joints 14.6 proximally abut distal arms 2.9 of the rear case 2.2. This prevents axial movement of the collar 14 in the proximal direction P. The joints 14.6 may be snap-fit joints.

Figure 10B:
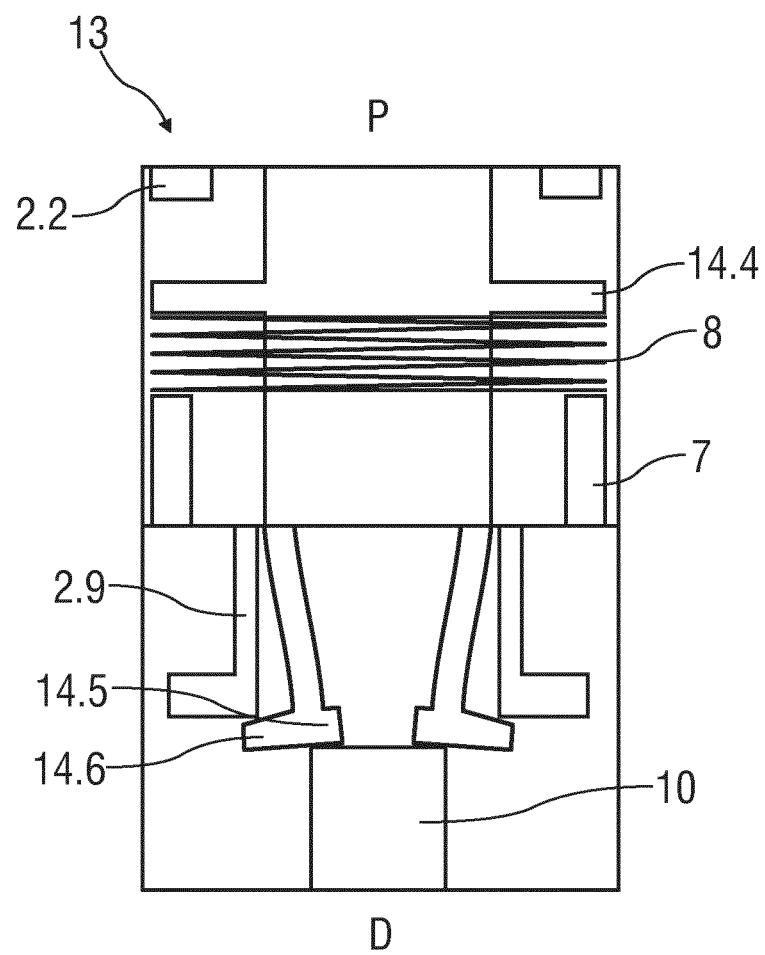
FIG. 10B is a schematic view of the feedback mechanism in a state during triggering of a feedback.

FIG. 10B shows the feedback mechanism 13 in a state when the feedback is triggered near the end of medicament dispense. The plunger 10, approaching the end of its travel with the stopper 6 having nearly bottomed out in the syringe 3, slides beyond the inner protrusions 14.5 allowing for inward deflection of the snap-fit joints 14.6. The snap-fit joints 14.6 so far radially deflected outwards begin to go back inwards to their relaxed shape, gradually losing contact with the distal arms 2.9 on the rear case 2.2 and thus enabling the collar 14 to move in the proximal direction P under the force of the control spring 8. In the meantime, the needle shroud 7 has been pushed in the proximal direction P as the needle 4 was inserted in previous steps, thus compressing the control spring 8 even further.

Figure 10C:
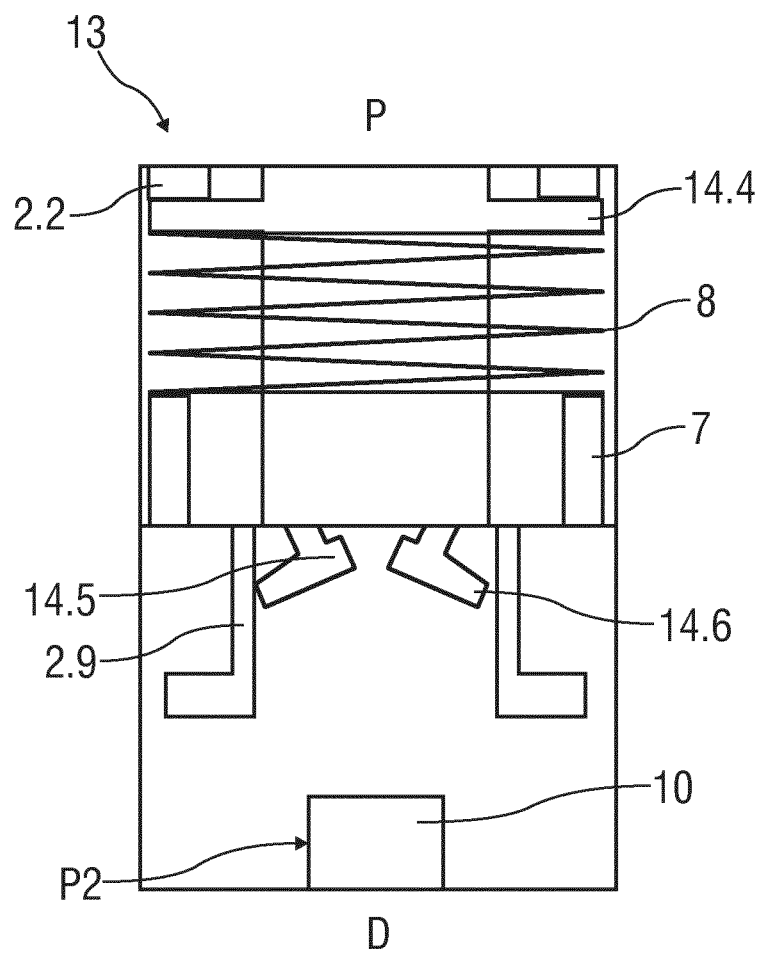
FIG. 10C is a schematic view of the feedback mechanism in a state after having generated the feedback.

FIG. 10C shows the feedback mechanism 13 in a state at the end of dose after having generated the feedback. The plunger 10 has finished its course in the syringe 3 barrel.

Immediately prior to this event, the two snap-fit joints 14.6 present on the collar 14 had become fully retracted inward decoupling from the distal arms 2.9 on the rear case 2.2. The collar 14 was thus propelled in the proximal direction P under the action of the control spring 8. The collar 14 hit the rear case 2.2, which created an audible and/or tactile feedback, e.g. a click noise indicating that the dose is complete.

In an exemplary embodiment, the feedback is triggered before the actual end of the dose.

Figure 11A:
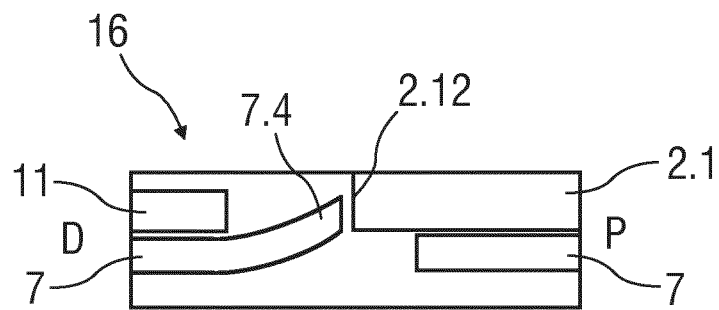
FIG. 11A is a schematic view of a second shroud lock mechanism.

FIG. 11A is a schematic view of a second shroud lock mechanism 16. The second shroud lock mechanism 16 is arranged to lock the needle shroud 7 after removal of the auto-injector 1 from an injection site post-use and consequent translation of the needle shroud 7 in the distal direction D relative the case 2 into a distal position S1, e.g. a second extended position. The second shroud lock mechanism 16 comprises at least one radially outwardly biased compliant shroud beam 7.4 on the needle shroud 7 adapted to proximally abut a stop 2.12 on the front case 2.1, preventing further movement of the needle shroud 7 in the proximal direction P relative the front case 2.1. The cap 11 is adapted to radially inwardly deflect the compliant shroud beam 7.4 when telescoped over the needle shroud 7, allowing the shroud beam 7.4 to pass the stop 2.12 in the proximal direction P so that the needle shroud 7 can move further in the proximal direction P relative the front case 2.1.

Figure 11B:
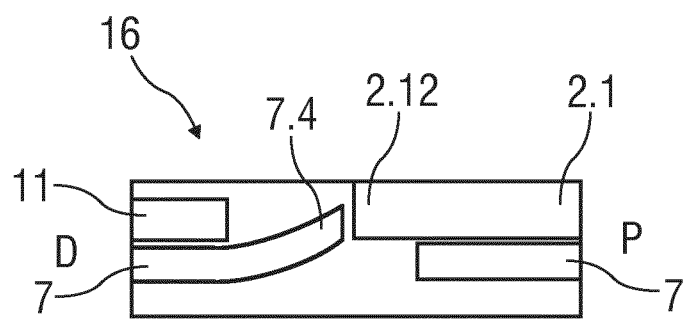
FIG. 11B is a schematic view of a second shroud lock mechanism.

FIG. 11B is a schematic view of the second shroud lock mechanism 16 after assembly of the control subassembly 1.1. The needle shroud 7 is partially inserted into the cap 11. The shroud beam 7.4 is relaxed and proximally abuts the stop 2.12 in the front case 2.1. This prevents the needle shroud 7 from moving further in the proximal direction P relative the front case 2.1 and keeps the control subassembly 1.1 locked together.

Figure 11C:
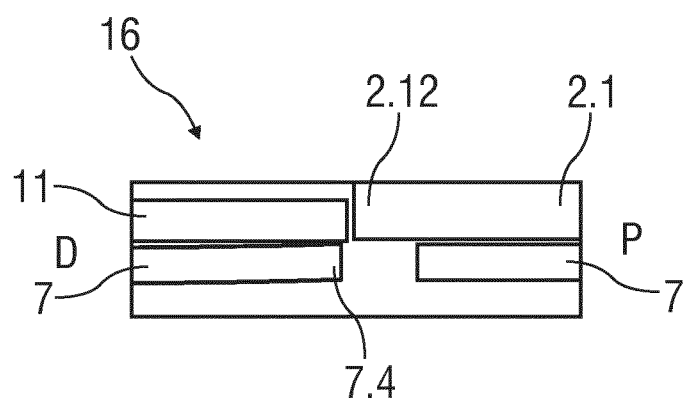
FIG. 11C is a schematic view of a second shroud lock mechanism.

FIG. 11C is a schematic view of the second shroud lock mechanism 16 during insertion of the syringe 3 into the control subassembly 1.1, wherein the needle shroud 7 is moved further in the distal direction D into the cap 11 such that the cap 11 inwardly deflects the shroud beam 7.4 out of its abutment with the stop 2.12. The needle shroud 7 is thus free to move in the proximal direction P relative the front case 2.1.

Figure 11D:
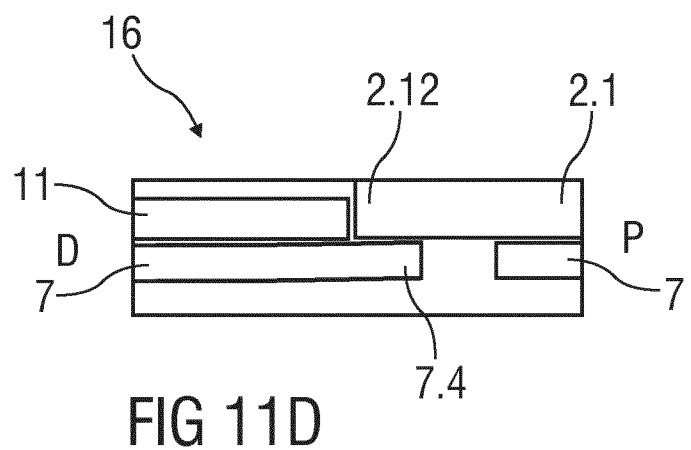
FIG. 11D is a schematic view of a second shroud lock mechanism.

FIG. 11D is a schematic view of the second shroud lock mechanism 16 after final assembly of the drive subassembly 1.2 to the control subassembly 1.1. The needle shroud 7 has been moved further in the proximal direction P relative the front case 2.1, e.g. by an assembly jig (not illustrated). In this state, the drive subassembly 1.2 may be assembled to the control subassembly 1.1. Subsequently, the assembly jig is removed and the needle shroud 7 allowed returning in the distal direction D relative the front case 2.1 under load of the shroud spring 8. However, this movement is limited by the plunger release mechanism 12. The needle shroud 7 is therefore in the position of FIG. 11D with the shroud beam 7.4 radially outwardly supported by the stop 2.12 in the front case 2.1 preventing deflection of the shroud beam 7.4.

Figure 11E:
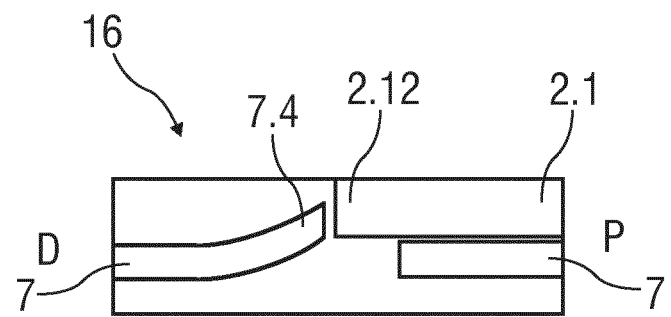
FIG. 11E is a schematic view of a second shroud lock mechanism.

FIG. 11E is a schematic view of the second shroud lock mechanism 16 having locked the needle shroud 7 in the distal position S1. As the needle shroud 7 is being moved from the retracted position RP towards the distal position S1, the shroud beam 7.4 passes the stop 2.12 in the distal direction D and relaxes radially outwards, which is possible as the cap 11 is no longer present. Afterwards the shroud beam 7.4 cannot return in the proximal direction P as it would hit the stop 2.12. The needle shroud 7 is thus locked in the distal position S1. Further extension of the needle shroud 7 may be prevented by a case boss on the case 2 engaging with a shroud boss in the needle shroud 7 (not illustrated).

Figure 12A:
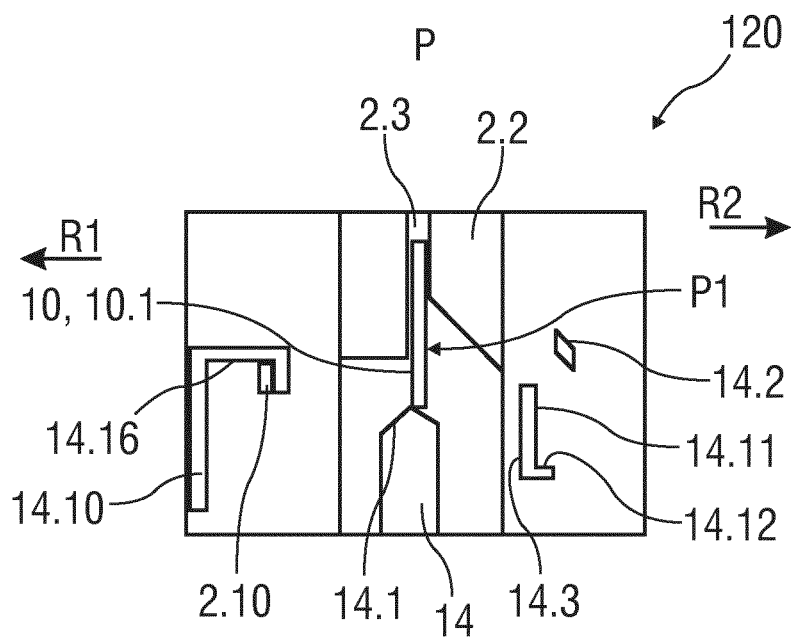
FIG. 12A is a schematic view of another exemplary embodiment of a plunger release mechanism during assembly.

FIG. 12A is a schematic view of another exemplary embodiment of a plunger release mechanism 120 in which the function of the second shroud lock mechanism is integrated. The plunger release mechanism 120 comprises the plunger 10, the rear case 2.2, the needle shroud 7 and the collar 14.

The needle shroud 7 and the plunger 10 are configured to move only in an axial direction, i.e. in the distal direction D and the proximal direction P, whereas the collar 14 can only move rotationally in the rotational directions R1, R2 and axially in the proximal direction P. The rear case 2.2 is fixed. In an exemplary embodiment, there may be no compliant part in the plunger release mechanism 120, i.e. the parts may be all rigid and move as a whole with no relative deformation within a part.

FIG. 12A shows the plunger release mechanism 120 in a pre-assembly state with the plunger 10 in a proximal position P1. In the pre-assembly state, a boss 10.1 on the plunger 10 is sited on a cam surface 14.1, e.g. an extruded path, within the collar 14, which prevents the plunger 10 from moving in the distal direction D when a force in the distal direction D is applied to the plunger 10, e.g. by the drive spring 9. The cam surface 14.1 comprises two angled ramps defining a tip between them. The angle of the ramp of the cam surface 14.1 on which the boss 10.1 is sited induces a small torque forcing the plunger 10 to rotate in the second rotational direction R2 and the collar 14 to slightly rotate in the opposite first rotational direction R1. The rotation of the plunger 10 in the first rotational direction R1 is stopped by the plunger boss 10.1 being engaged in a longitudinal slot 2.3 in the rear case 2.2. The rotation of the collar 14 in the first rotational direction R1 is stopped by an interface 14.10 on the collar 14 engaging a case rib 2.10 on the rear case 2.2. The interface 14.10 comprises two lateral surfaces 14.14, 14.15 adapted to operatively abut the case rib 2.10 allowing for a limited rotation of the collar 14 relative to the rear case 2.2. Furthermore, the interface 14.10 comprises a distal surface 14.16 adapted to abut the case rib 2.10 preventing movement of the collar 14 in the distal direction D.

The axial load from the drive spring 9 biasing the plunger 10 in the distal direction D is coupled from the plunger 10 to the collar 14 through the plunger boss 10.1 and the cam surface 14.1 and further from the collar 14 to the rear case 2.2 through the interface 14.10 and the case rib 2.10. The control spring 8 is arranged between the collar 14 and the needle shroud 7, thus biasing the collar 14 in the proximal direction P. As the drive spring 9 load is far greater than the control spring 8 load, the collar 14 is held in the position of FIG. 12A with respect to the rear case 2.2.

Figure 12B:
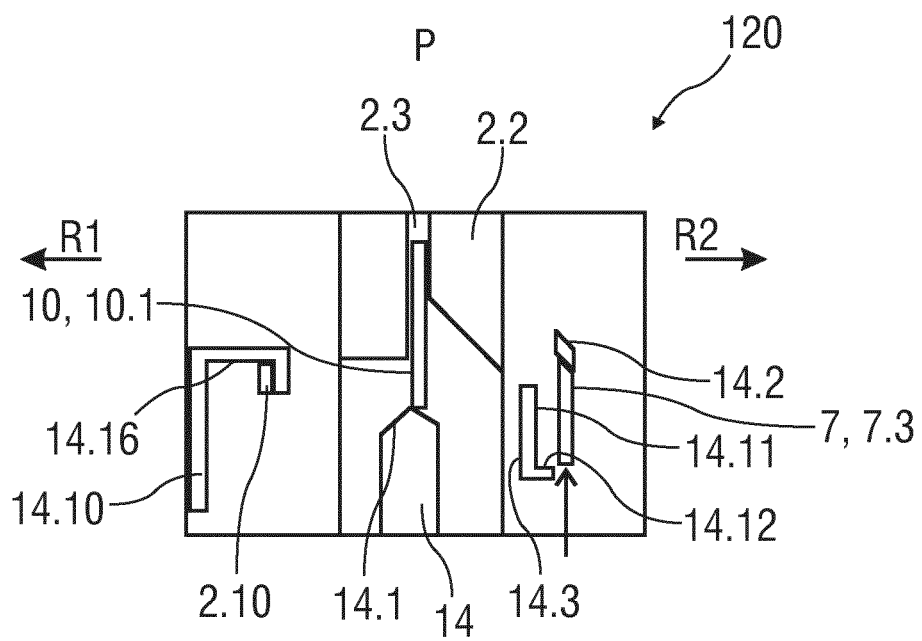
FIG. 12B is a schematic view of the plunger release mechanism during assembly.

FIG. 12B shows the plunger release mechanism 12 in a state during insertion of the drive sub-assembly 1.2 into the control sub-assembly 1.1. A shroud boss 7.3 on the shroud 7 comes into contact with a first collar rib 14.2 on the collar 14. The shroud boss 7.3 and the first collar rib 14.2 are designed so that the proximal motion of the shroud 7 causes the collar 14 to slightly rotate in the second rotational direction R2. This sets the plunger boss 10.1 in an unstable position on a tip of the cam surface 14.1. In the illustrated embodiment, the first collar rib 14.2 is angled to achieve this. In other embodiments, the shroud boss 7.3 may be angled instead of the first collar rib 14.2. Likewise, both the first collar rib 14.2 and the shroud boss 7.3 may be angled. As the rotation of the collar 14 continues, the cam surface 14.1 interfacing with the plunger boss 10.1 transitions to an inverted angle which reverses the direction of torque applied to the collar 14. The rotation of the collar 14 then continues without the force applied by the needle shroud 7.

Figure 12C:
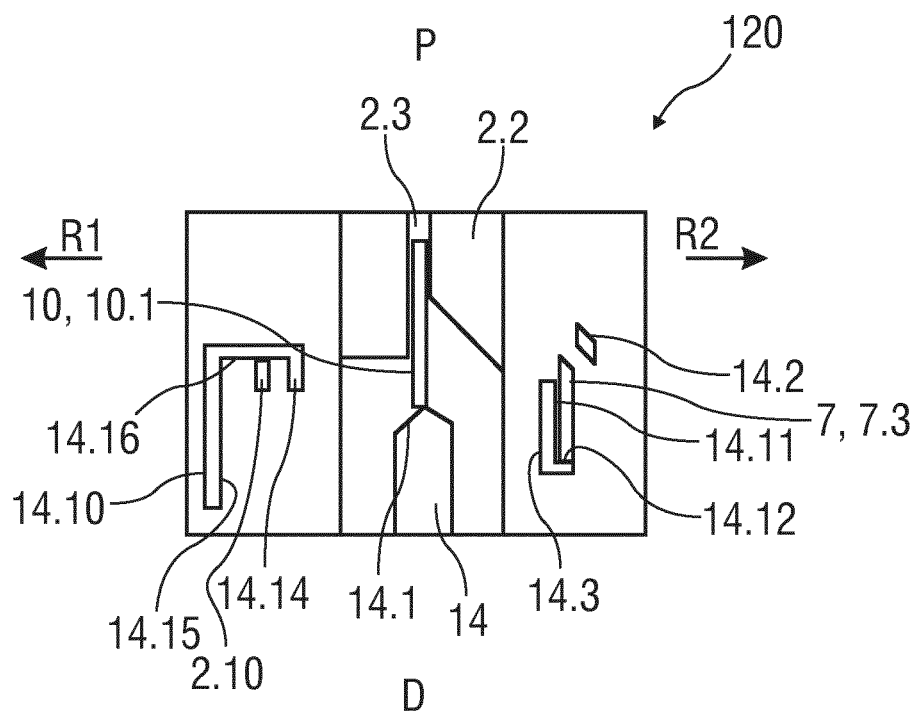
FIG. 12C is a schematic view of the plunger release mechanism in a pre-use state.

FIG. 12C shows the plunger release mechanism 12 in a pre-use state. The collar 14 keeps rotating in the second rotational direction R2 under the action of the needle shroud 7. In addition, the plunger 10, driven by the drive spring 9, now fosters the rotation of the collar 14 as well, as the plunger boss 10.1 starts to fall along the cam surface 14.1 on the collar 14. The rotational motion of the collar 14 in the second rotational direction R2 is stopped when the shroud boss 7.3 laterally abuts a first longitudinal surface 14.11 of an L-shaped second collar rib 14.3. As the plunger boss 10.1 still sits on the cam surface 14.1 of the collar 14, the plunger 10 is prevented from being released. The shroud boss 7.3 engages proximally behind a transversal surface 14.12 of the L-shaped second collar rib 14.3 preventing subsequent movement of the needle shroud 7 in the distal direction D relative to the collar 14.

The plunger release mechanism 120 is in its pre-use configuration.

Figure 12D:
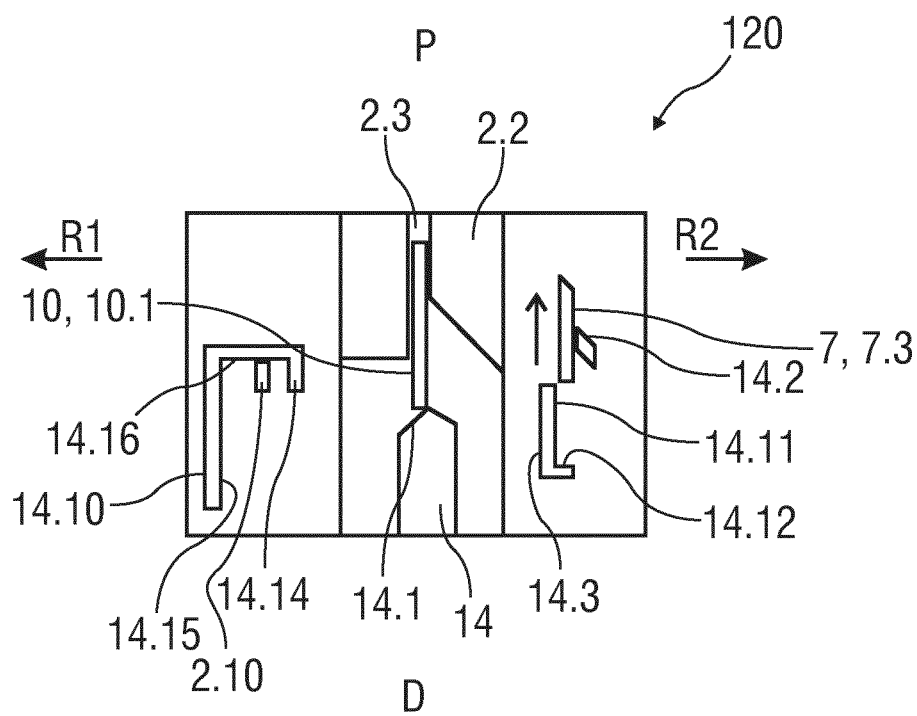
FIG. 12D is a schematic view of the plunger release mechanism during depression of a needle shroud.

FIG. 12D shows the plunger release mechanism 120 in a state during depression of the needle shroud 7. The needle shroud 7 is moved in the proximal direction P into the front case 2.1, e.g. by a user pressing the needle shroud 7 against an injection site, thereby inserting the needle 4 into the injection site. During this motion, the shroud boss 7.3 moves in the proximal direction P along the first longitudinal surface 14.11 of the L-shaped second collar rib 14.3. When full needle insertion depth is reached, the shroud boss 7.3 travels beyond a proximal end of the first longitudinal surface 14.11 of the second collar rib 14.3. The plunger boss 10.1 biased by the drive spring 9 in the distal direction D and acting on the cam surface 14.1 thus rotates the collar 14 further in the second rotational direction R2.

Figure 12E:
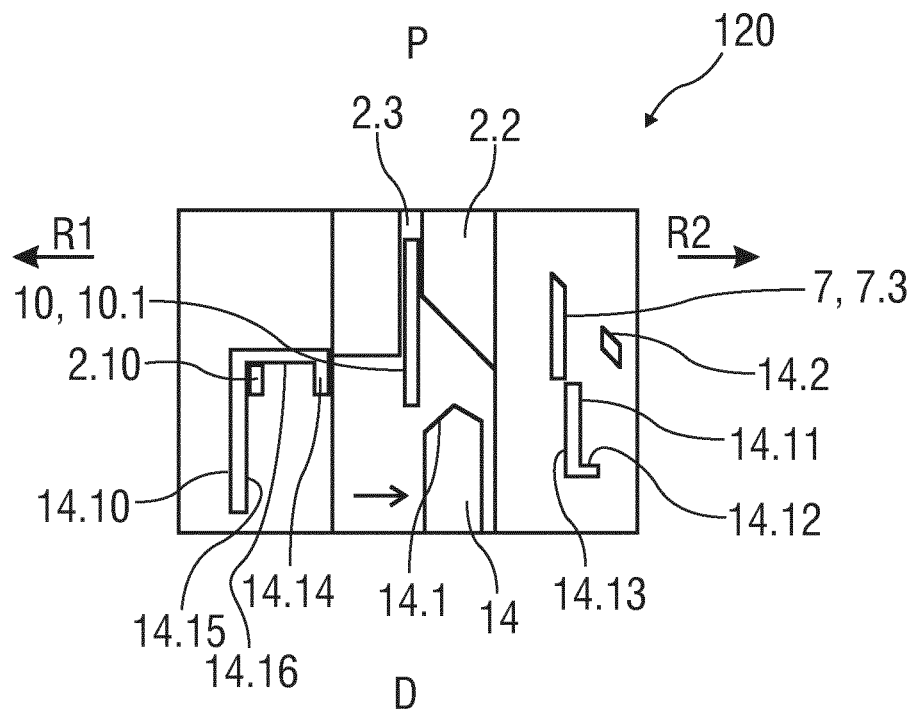
FIG. 12E is a schematic view of the plunger release mechanism during release of a plunger.

FIG. 12E shows the plunger release mechanism 120 in a state during release of the plunger 10. The collar 14 has continued rotating until the plunger boss 10.1 reaches the end of the cam surface 14.1, allowing the plunger 10 to move in the distal direction D without being further subjected to torque. As the collar 14 is no longer biased in the distal direction D by the drive spring 9 through the plunger boss 10.1 acting on the cam surface 14.1, the collar 14 is now free to move in the proximal direction P under the action of the control spring 8 force with respect to the needle shroud 7. This travel is limited by the feedback mechanism 13 as illustrated in FIG. 10A. As the collar 14 was rotated while the needle shroud 7 remained rotationally fixed, the shroud boss 7.3 which was previously aligned with the first longitudinal surface 14.11 of the L-shaped second collar rib 14.3 pointing in the second rotational direction R2 is now aligned with an opposite second longitudinal surface 14.13 of the L-shaped second collar rib 14.3 pointing in the first rotational direction R1.

Figure 12F:
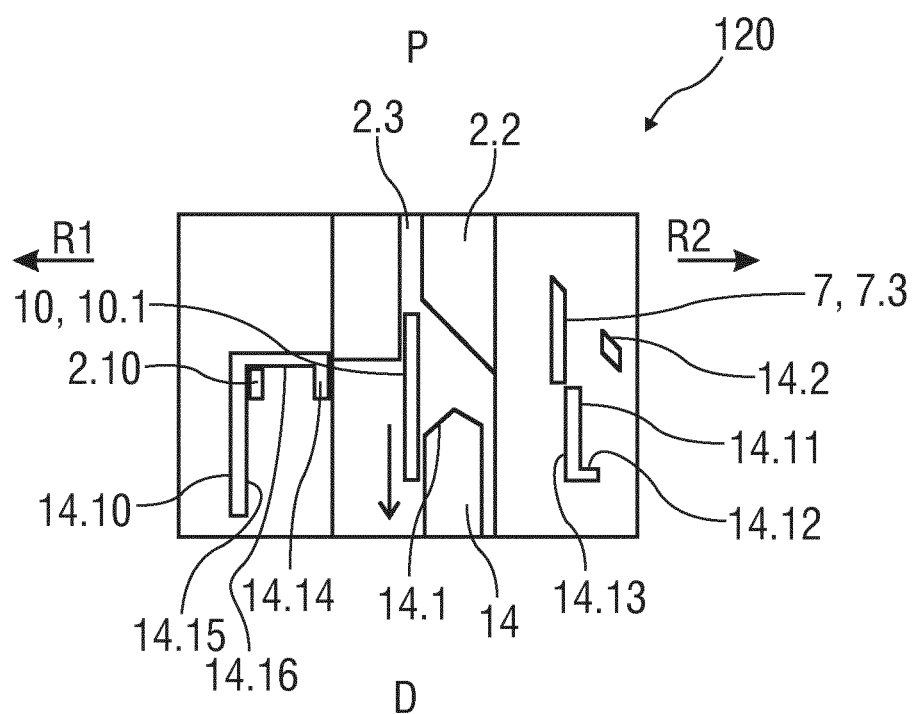
FIG. 12F is a schematic view of the plunger release mechanism during an injection stroke of the plunger.

FIG. 12F shows the plunger release mechanism 120 in a state during drug delivery. Under the action of the drive spring 9, the plunger 10 pushes on the stopper 6 and starts to empty the content of the syringe 3.

Figure 12G:
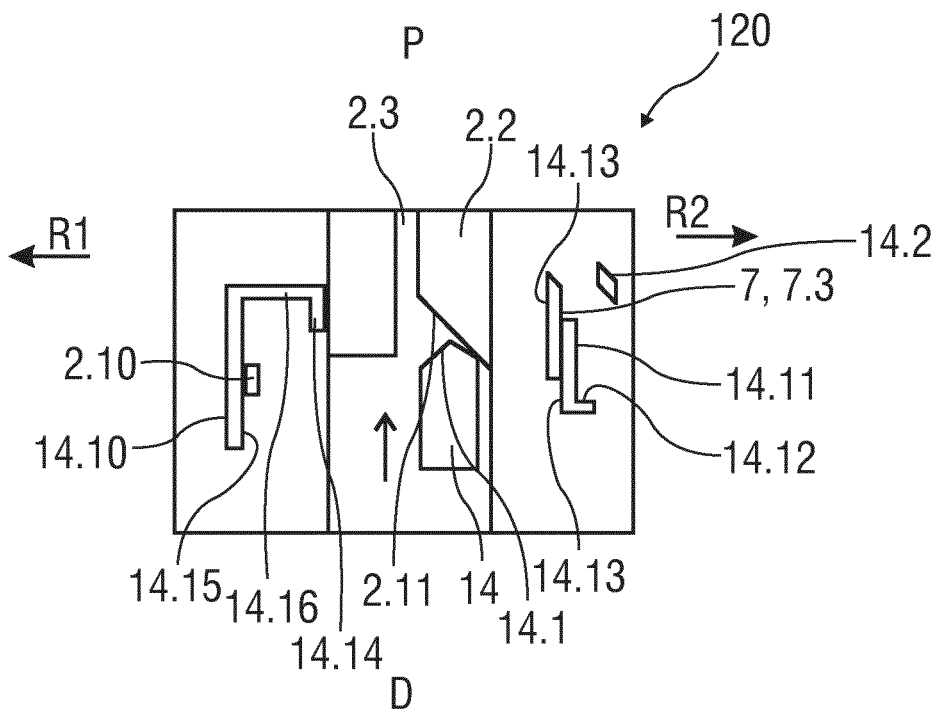
FIG. 12G is a schematic view of the plunger release mechanism at the end of the injection stroke.

FIG. 12G is a schematic view of the plunger release mechanism 120 near the end of the injection stroke. The feedback mechanism 13, as illustrated in FIG. 10B, releases the collar 14 allowing it to move in the proximal direction P under the action of the control spring 8. The collar 14, e.g. the cam surface 14.1, abuts a ramped surface 2.11 on the rear case 2.2. This contact creates an audible and or tactile feedback indicating that the dose is nearly complete. The ramped surface 2.11 on the rear case 2.2 imparts a torque on the collar 14 in the first rotational direction R1. As the collar 14 was moved in the proximal direction P while the needle shroud 7 remained in its axial position, the shroud boss 7.3 abuts the second longitudinal surface 14.13 of the L-shaped second collar rib 14.3 pointing in the first rotational direction R1. The torque on the collar 14 is thus resolved by the contact between the shroud boss 7.3 and the second collar rib 14.3.

Figure 12H:
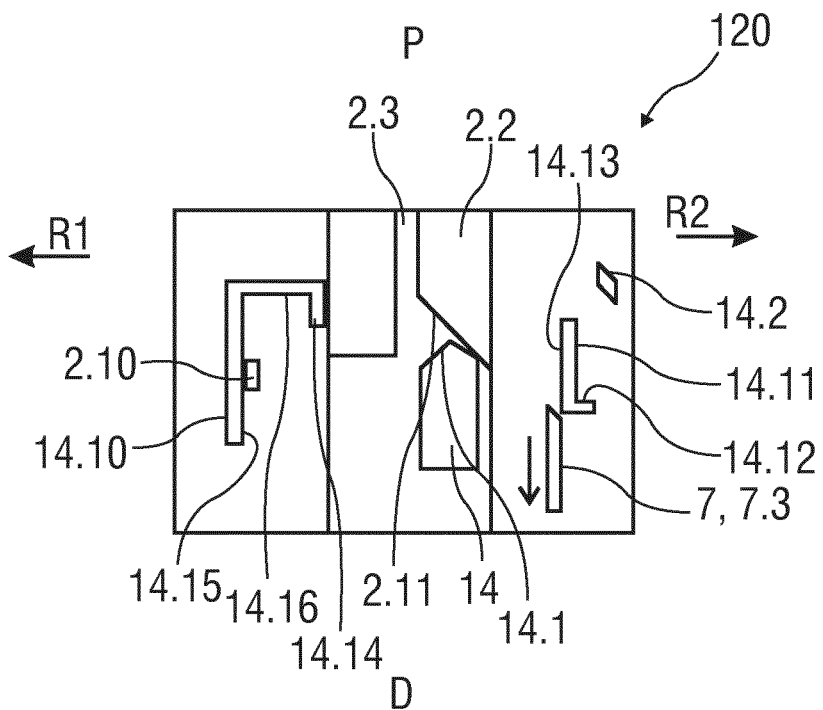
FIG. 12H is a schematic view of the plunger release mechanism after the injection stroke during extension of the needle shroud.

FIG. 12H is a schematic view of the plunger release mechanism 120 after the injection stroke during extension of the needle shroud 7. When the auto-injector 1 is removed from the injection site, the needle shroud 7 extends in the distal direction D under the action of the control spring 8. This motion continues until the shroud boss 7.3 is no longer in support of the second collar rib 14.3. At this point, the needle shroud 7 is fully extended.

Figure 12J:
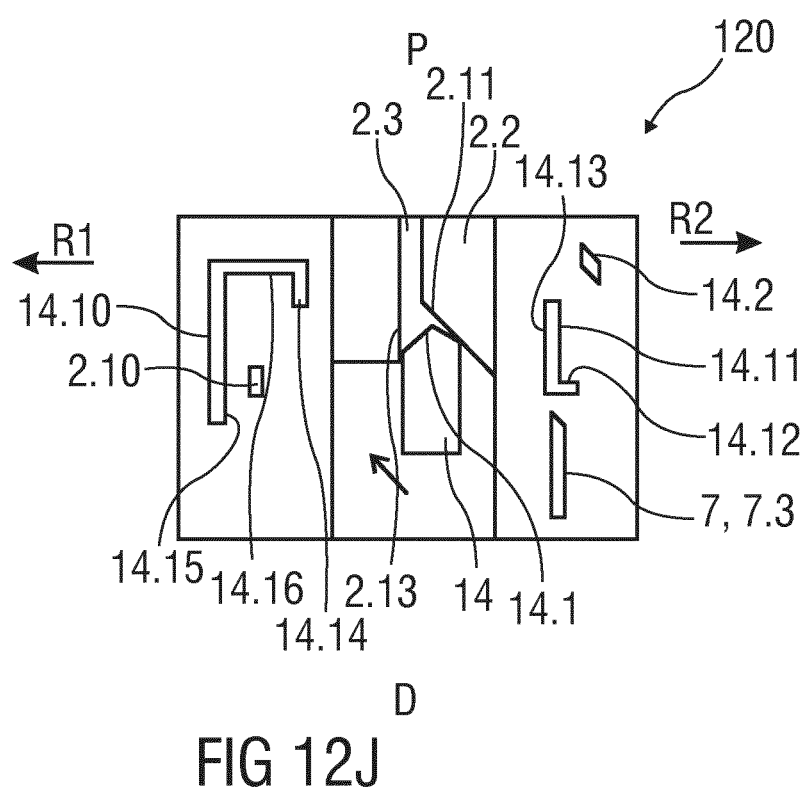
FIG. 12J is a schematic view of the plunger release mechanism having locked out the extended needle shroud.

FIG. 12J is a schematic view of the plunger release mechanism 120 in a post-use state having locked out the extended needle shroud 7. As the shroud boss 7.3 is no longer supporting the second collar rib 14.3, the torque applied to the collar 14 through the engagement of the cam surface 14.1 on the ramped surface 2.11 rotates the collar 14 in the first rotational direction R1. This rotation continues until the cam surface 14.1 comes into contact with an angular stop 2.13 in the rear case 2.2 which prevents further rotation. In this position, the second collar rib 14.3 is aligned in the axial path of the shroud boss 7.3. Therefore, if it is attempted to push the needle shroud 7 in the proximal direction P again, the travel is blocked by the collar 14. This creates a shroud lock preventing further depression of the needle shroud 7 and re-exposure of the needle 4.

A sequence of operation of the auto-injector 1 is as follows:

The auto-injector 1 is initially in the state as shown in FIG. 1. The plunger release mechanism 12 is in the pre-use state as shown in FIG. 8D. The feedback mechanism 13 is in the pre-use state as illustrated in FIG. 8B. The first shroud lock mechanism 15 is in the pre-use state as illustrated in FIG. 10A. If the alternative plunger release mechanism 120 is applied, it is in the pre-use state of FIG. 12C.

Figure 13:
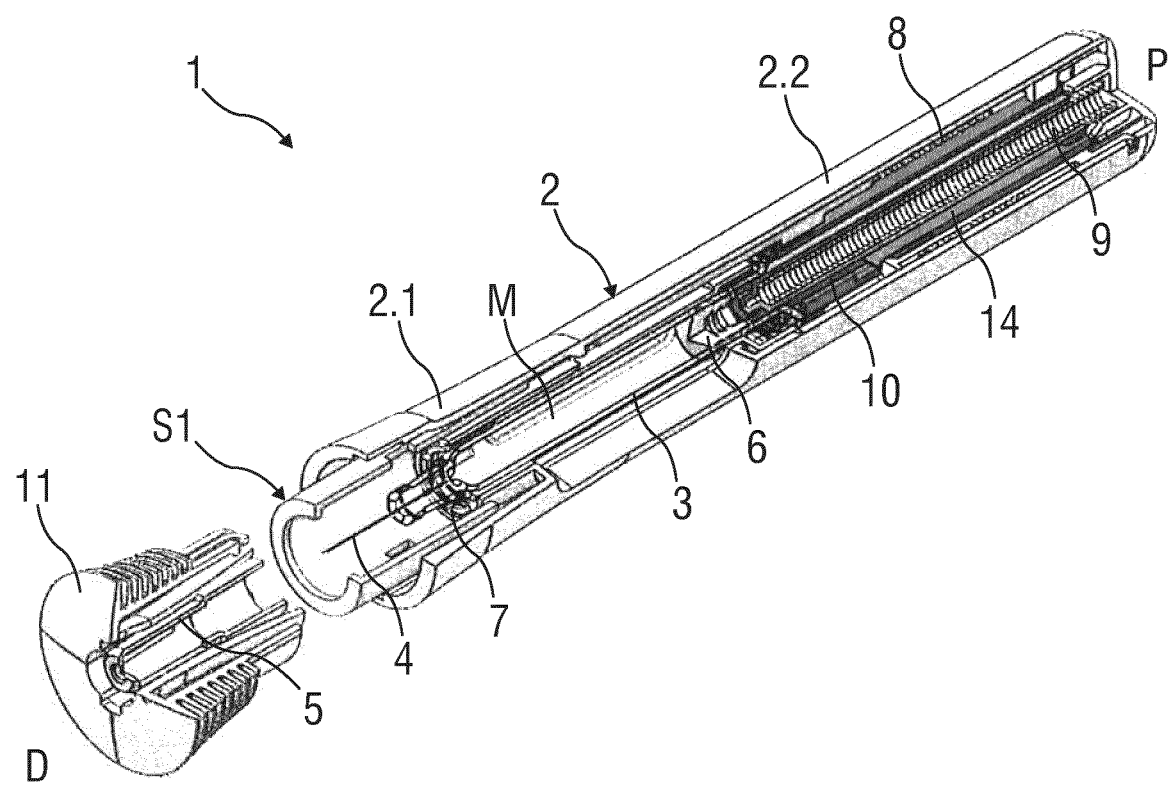
FIG. 13 is a perspective longitudinal section of the auto-injector with the cap removed.

The user removes the cap 11 pulling it in the distal direction D away from the case 2. The protective needle sheath 5 may be coupled to the cap 11 so that when the cap 11 is removed, the protective needle sheath 5 is also removed from the needle 4. FIG. 13 is a perspective longitudinal section of the auto-injector 1 with the cap 11 removed. The needle shroud 7 is in a distal position S1.

Figure 14:
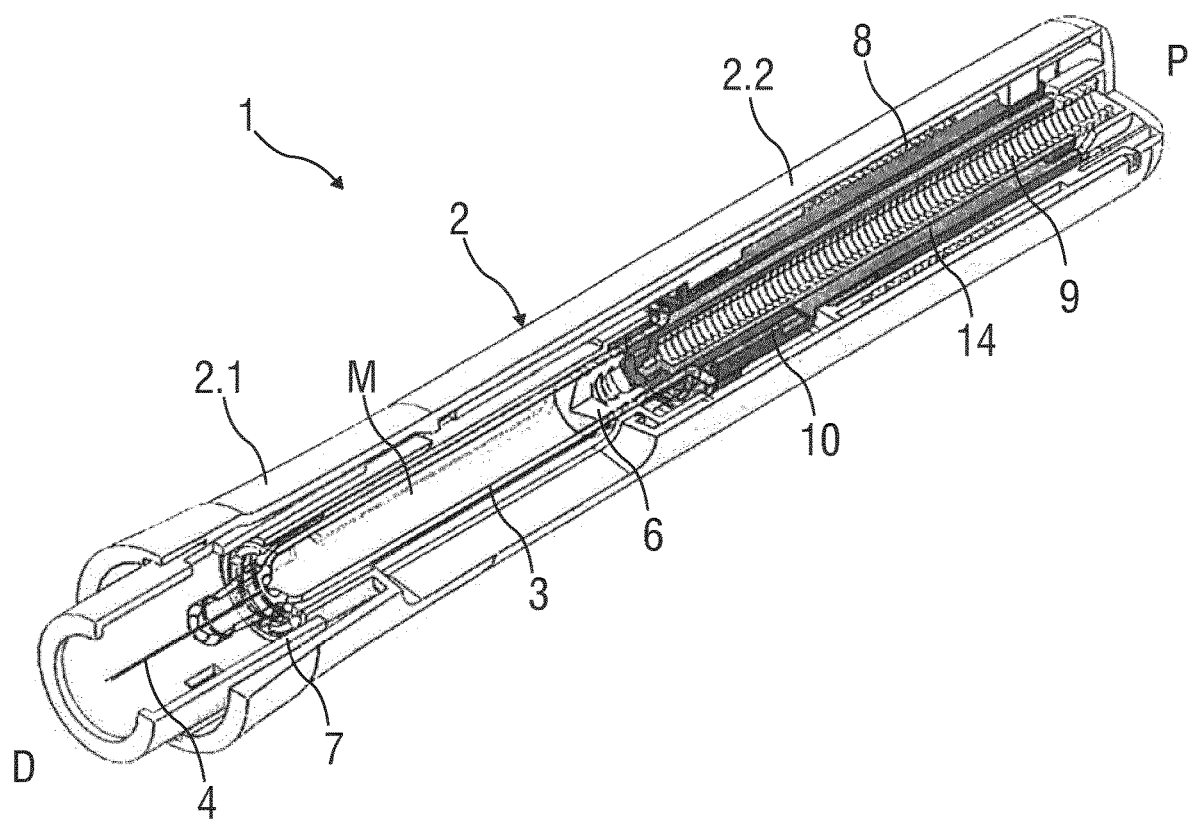
FIG. 14 is a perspective longitudinal section of the auto-injector with the needle shroud being moved in the proximal direction.

FIG. 14 is a perspective longitudinal section of the auto-injector 1 with the needle shroud 7 being moved in the proximal direction P, e.g. by placing it against the injection site and sliding the case 2 forwards. The control spring 8 is held between the collar 14 and the needle shroud 7 and is further compressed when the case 2 moves forwards relative to the needle shroud 7. Except for the needle shroud 7, all components of the auto-injector 1 move with the case 2. The needle shroud 7 moves in the proximal direction P in comparison to the rest of the parts of the auto-injector 1, thus initiating the plunger release mechanism 12 or 120. The plunger release mechanism 12 thus arrives in the state as illustrated in FIG. 8E. If the alternative plunger release mechanism 120 is applied, it arrives in the state as illustrated in FIG. 12D.

Figure 15:
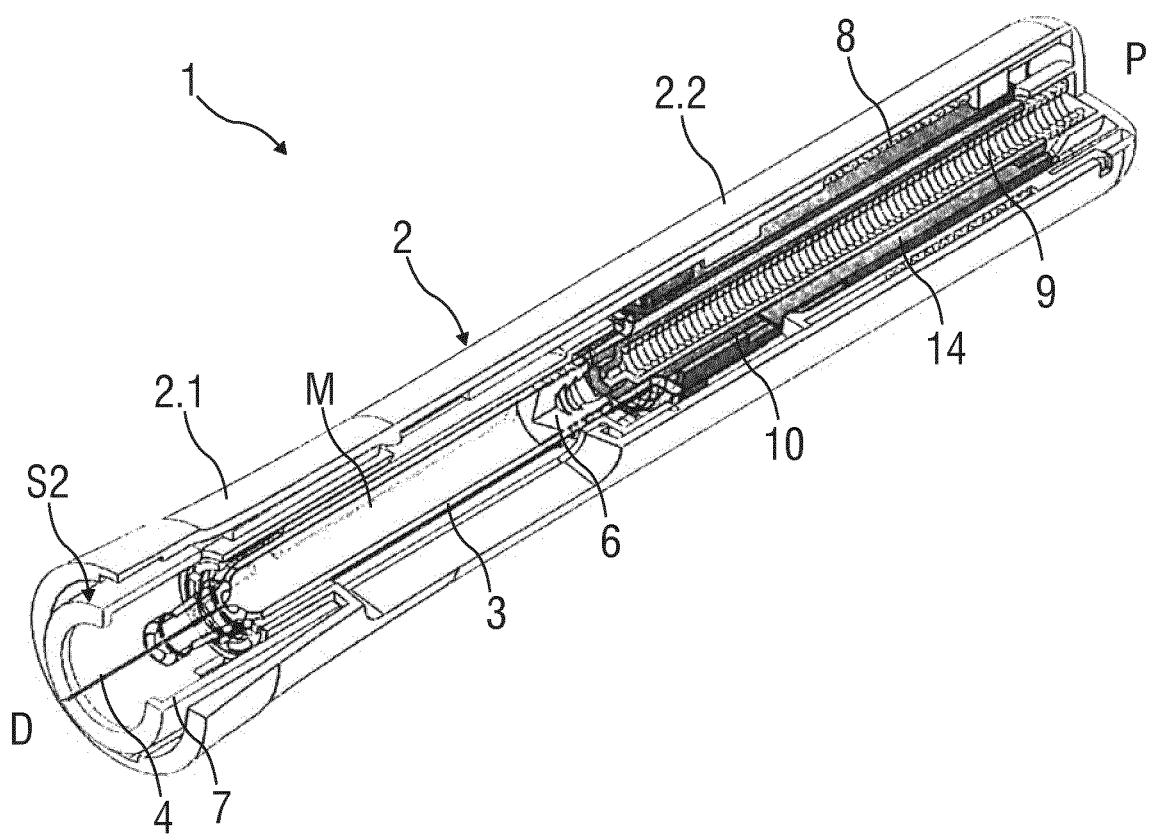
FIG. 15 is a perspective longitudinal section of the auto-injector with the needle shroud in a proximal position.

FIG. 15 is a perspective longitudinal section of the auto-injector 1 with the needle shroud 7 being fully moved in the proximal direction P into a proximal position S2 such that the needle 4 has reached the insertion depth in the injection site. Once the needle shroud 7 is fully depressed, the plunger 10 releases as shown in FIG. 8E and medicament delivery begins. The drive spring 9 begins to expand, pushing the plunger 10 in the distal direction D to inject the medicament M. If the alternative plunger release mechanism 120 is applied, the plunger 10 releases as shown in FIG. 12E.

Figure 16:
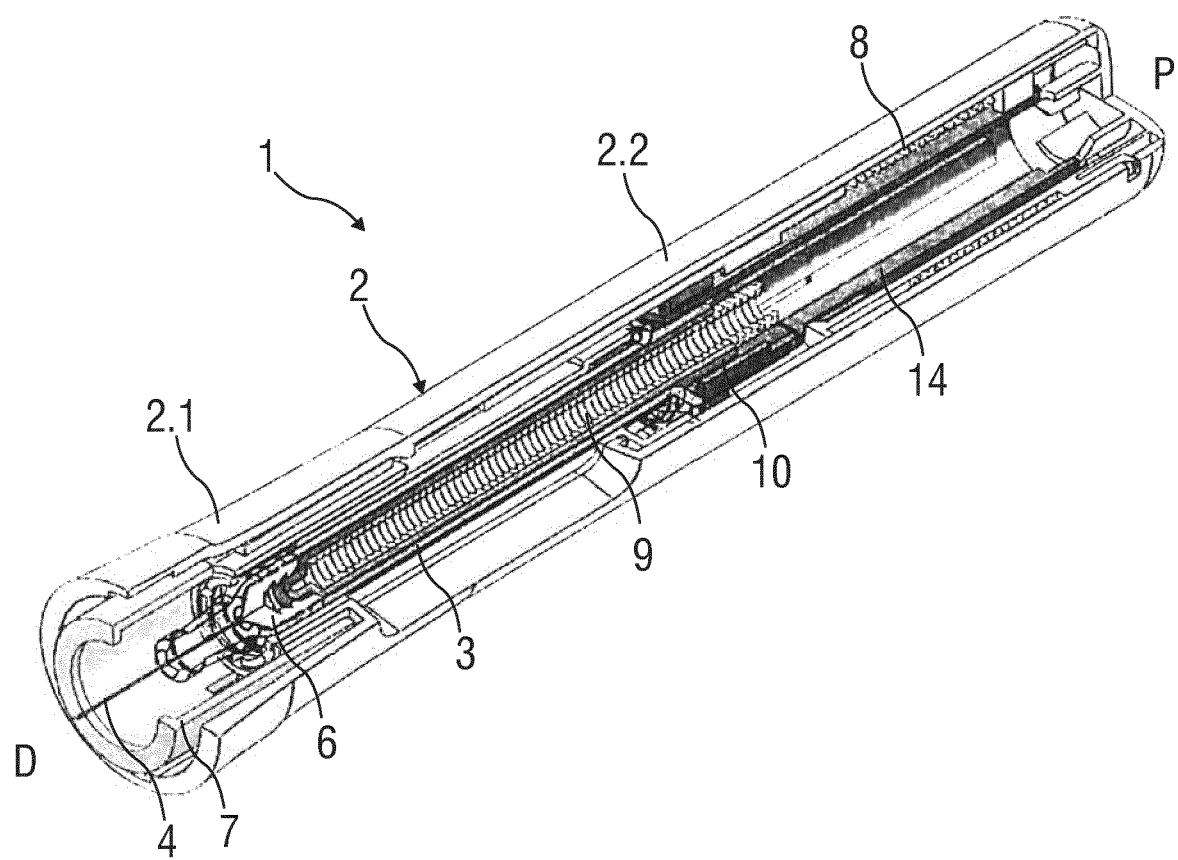
FIG. 16 is a perspective longitudinal section of the auto-injector during delivery of the medicament after release of the feedback mechanism.

FIG. 16 is a perspective longitudinal section of the auto-injector 1 during delivery of the medicament M after release of the feedback mechanism 13. As the delivery of the medicament M progresses with the plunger 10 moving down the syringe 3 barrel, the feedback mechanism 13 activates. The feedback mechanism 13 arrives in the state as illustrated in FIG. 10B.

Figure 17:
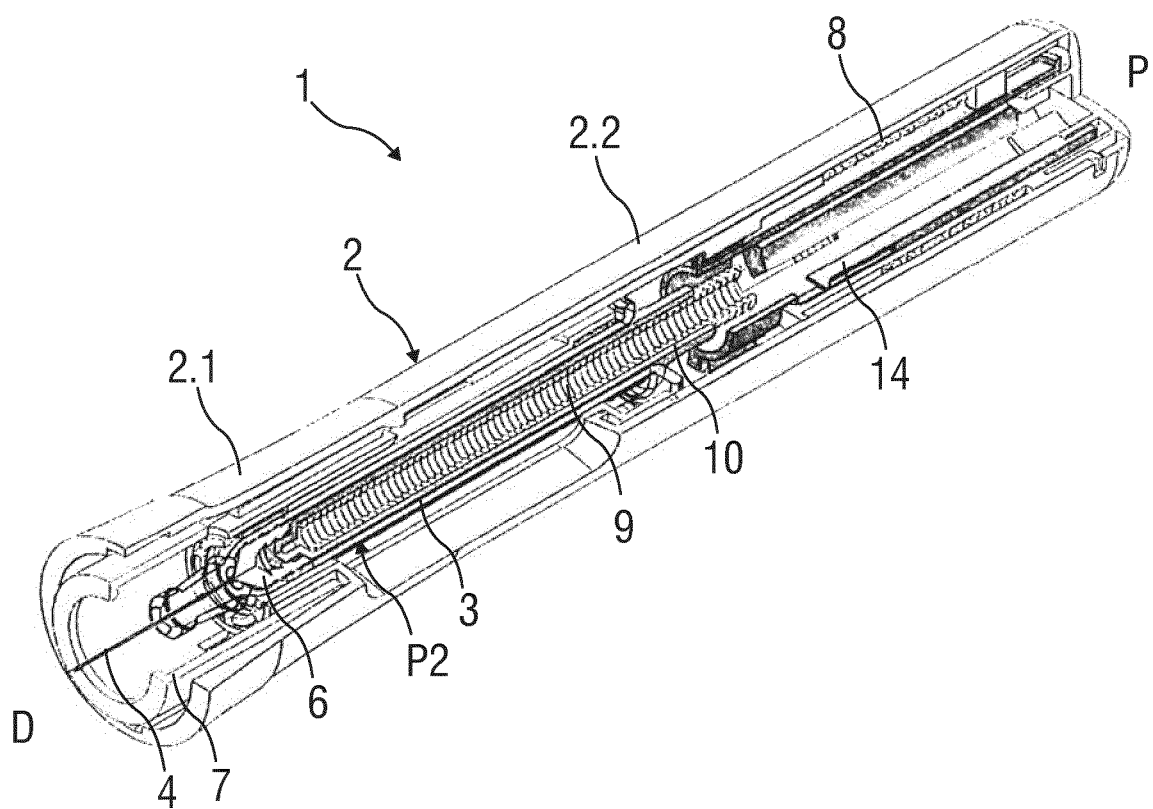
FIG. 17 is a perspective longitudinal section of the auto-injector at the end of dose after generation of the audible feedback.

FIG. 17 is a perspective longitudinal section of the auto-injector 1 at the end of dose prior to generation of the audible feedback. The feedback mechanism 13 arrives in the state as illustrated in FIG. 10C. The plunger 10 fully advances the stopper 6 within the syringe 3 barrel and arrives at a distal position P2. The injection is complete and an audible and/or tactile feedback is emitted through the collar 14 hitting the rear case 2.2 as the feedback mechanism 13 operates.

If the auto-injector 1 is moved away from the injection site, the needle shroud 7 advances in the distal direction D, driven by the control spring 8. The needle shroud 7 returns to its pre-use position. The second shroud lock 16 arrives in the state as shown in FIG. 11E, locking the needle shroud 7 in its axial position. If the alternative plunger release mechanism 120 with inherent shroud lock is applied, it transitions through the state of FIG. 12H and arrives in the state as shown in FIG. 12J.

Figure 18:
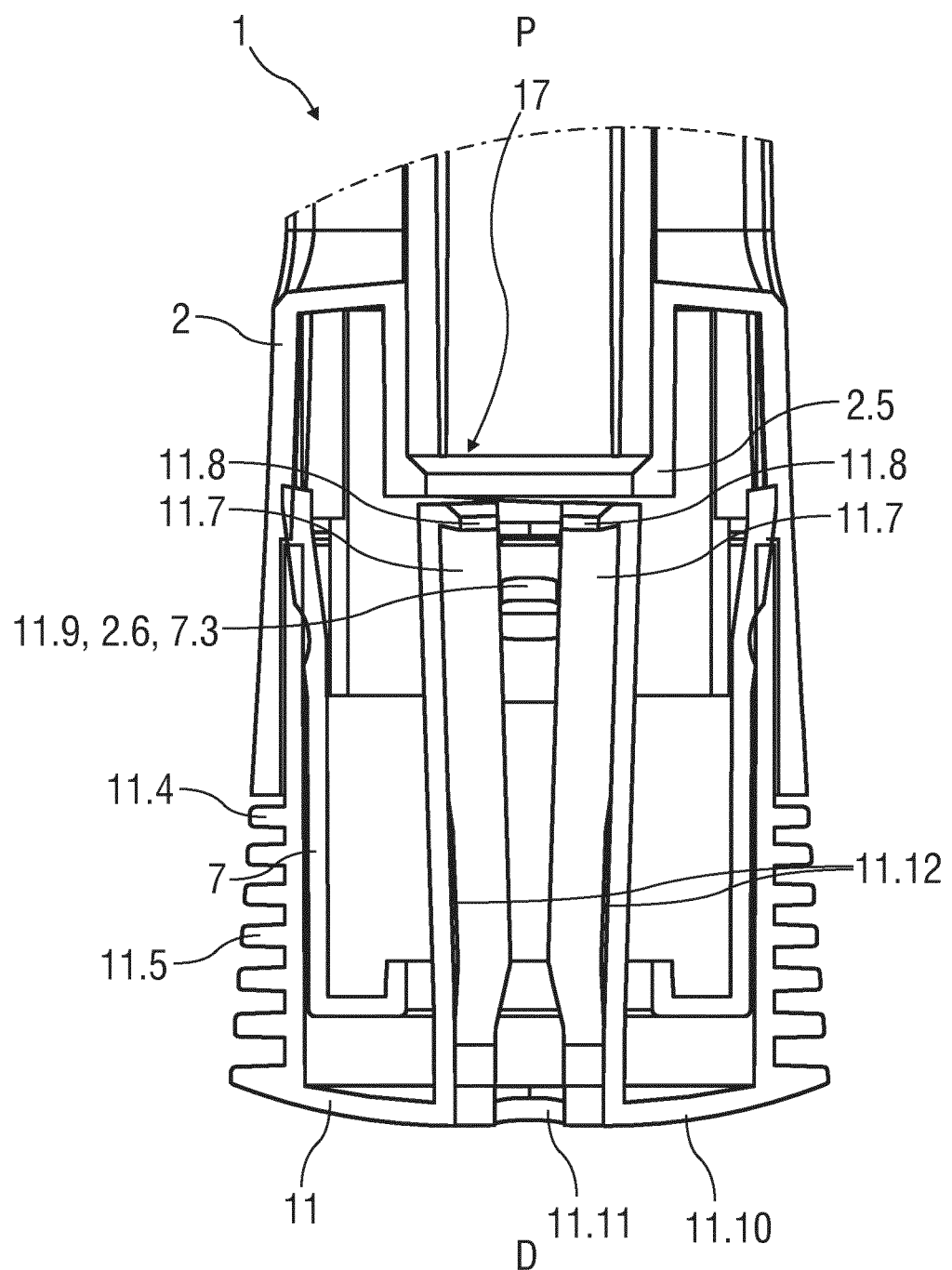
FIG. 18 is a longitudinal section of a distal end of the auto-injector with a sheath removal mechanism comprising a cap.

FIG. 18 is a longitudinal section of a distal end of the auto-injector 1 with a needle sheath removal mechanism 17 comprising a cap 11. The needle sheath removal mechanism 17 may be applied in the above described auto-injector 1.

In an exemplary embodiment, the cap 11 may be removably disposed at a distal end of the case 2. The cap 11 may include an element (e.g., a barb, a hook, a narrowed section, etc.) arranged to engage the case 2, a needle shroud 7 telescoped within the case 2, and/or a protective needle sheath 5 on the needle 4. The protective needle sheath 5 may be rubber and/or plastic. In an exemplary embodiment, the protective needle sheath 5 is a rigid needle shield (RNS) formed from a rubber interior adapted to engage the needle 4 with a plastic exterior at least partially covering an outer portion of the rubber interior. The cap 11 may comprise grip features 11.5 for facilitating removal of the cap 11 (e.g., by twisting and/or pulling the cap 11 relative to the case 2). In an exemplary embodiment, the grip features 11.5 may include one or more ribs, ridges, projections, bumps, notches, textured surfaces, or an overmolded coating (rubber, elastic, etc.), etc.

In an exemplary embodiment, a sheath removal mechanism 17 is arranged to remove the protective needle sheath 5 from the medicament container 3 on removal of the cap 11 from the autoinjector 1. The sheath removal mechanism 17 may comprise one or more compliant sheath removal beams 11.7 on the cap 11 adapted to engage the protective needle sheath 5. Typically, the sheath removal beams 11.7 extend in a proximal direction P from a distal face 11.10 of the cap 11 or are part of an internal sleeve extending in the proximal direction P from a distal face 11.10 of the cap 11. The compliant sheath removal beams 11.7 comprise respective inward ledges 11.8. When the compliant sheath removal beams 11.7 are relaxed, the ledges 11.8 provide a clearance between them smaller than a diameter of a protective needle sheath 5. In an exemplary embodiment, an assembly tool may be inserted in an axial direction through an opening 11.11 in the distal face 11.10 of the cap 11.

In another exemplary embodiment, one or more lateral apertures 11.9 are arranged in a lateral area of the cap 11 to allow insertion of an assembling tool. Corresponding lateral apertures may likewise be arranged in the case 2 and the needle shroud 7 in such a manner that a set of lateral apertures 11.9 respectively aligns when the cap 11 is attached to the case 2.

The cap 11 is assembled to the autoinjector 1 by being moved in a proximal direction P relative to the needle shroud 7. When the cap 11 is being attached to the autoinjector 1, the sheath removal beams 11.7 are inserted into the needle shroud 7 which is sufficiently wide to allow this.

When the cap 11 is attached to the autoinjector 1, axial movement of the cap 11 in the proximal direction P relative the case 2 is limited by a rib 11.4 on the cap 11 abutting the case 2.

The wedge-shaped assembly tool may engage between two of the sheath removal beams 11.7 splaying them apart, thereby deflecting them in a radial outward direction. This opens up the clearance defined by the inward ledges 11.8 to an extent allowing a protective needle sheath 5 to pass through. In an exemplary embodiment, the wedge-shaped assembly tool can also be arranged to displace the shroud 7 axially in the same motion enabling the engagement of the second shroud lock mechanism 16 and priming of the plunger release mechanism 12 or 120.

When the autoinjector 1 and/or the medicament container 3 are assembled, a protective needle sheath 5 may be removably coupled to the needle 4. The protective needle sheath 5 may be a rubber needle sheath or a rigid needle sheath (which is composed of rubber and a full or partial plastic shell). In other exemplary embodiments, the medicament container 3 may be a cartridge which includes the medicament M and engages a removable needle (e.g., by threads, snaps, friction, etc.).

The medicament container 3 and the protective needle sheath 5 are inserted into the case 2 and pushed in the distal direction D. Due to the assembly tool, the clearance between the ledges 11.8 on the compliant sheath removal beams 11.7 is wide enough to allow insertion of the protective needle sheath 5. In an exemplary embodiment, the case 2 may comprise an axial stop limiting axial movement of the medicament container 3 within the case 2 in the distal direction D, e.g. by engaging a neck portion of the medicament container 3. Likewise, the neck portion may be held by a carrier 18 and the carrier 18 may be held within the case 2 in a different way.

The assembly tool may then be removed from the opening 11.11 in the distal face 11.10 of the cap 11 such that the sheath removal beams 11.7 are no longer splayed apart. Due to their beam stiffness, the sheath removal beams 11.7 relax radially inwards, the inward ledges 11.8 reduce the clearance between them and engage a proximal end of the protective needle sheath 5, thus axially coupling the cap 11 to the protective needle sheath 5. In an exemplary embodiment, the sheath removal beams 11.7 are molded in an inward deflected position which ensures they are always in intimate contact with the protective needle sheath 5 once the tool is removed. The wedge-shaped assembly tool may be designed so that the sheath removal beams 11.7 are not deformed so far as to plastically yield. The contact point between the protective needle sheath 5 and the sheath removal beams 11.7 is arranged to minimize the moment acting to open the sheath removal beams 11.7 as the protective needle sheath 5 is removed. Hence, gripping of the protective needle sheath 5 does not rely on radial compressive force exerted by the sheath removal beams 11.7 but on a force exerted to the cap 11 in the distal direction D relative to the case 2. In an exemplary embodiment, the wedge-shaped assembly tool may be arranged to splay the sheath removal beams 11.7 in a direction perpendicular to the direction of the force exerted to the cap 11 during cap removal.

When the cap 11 is pulled in the distal direction D relative to the case 2, the ledges 11.8 engaged to the proximal end of the protective needle sheath 5 pull the protective needle sheath 5 off the medicament container 3. Post cap removal the protective needle sheath 5 may be retained by the ledges 11.8 and two small ribs 11.12 to prevent the protective needle sheath 5 falling out of the cap 11.

In an exemplary embodiment, a force required to press the needle shroud 7 may be approximately 2-12 N. Likewise, the mechanism may work with a higher force.

The case 2 may comprise a viewing window (not illustrated) allowing the user to examine the medicament M for clarity, observe the advancing plunger 10 for allowing to estimate the progress of the medicament delivery, and helping the user differentiate between a used and an un-used auto-injector 1.

In an exemplary embodiment, a tamper strip may be arranged between the cap 11 and the front case 2.1 when the control subassembly 1.1 is assembled.

The auto-injector 1 may be placed against the injection site multiple times without any adverse effect to the mechanism. The force to depress the needle shroud 7 may be less than 6 N.

The syringe 3 used in the auto-injector 1 may for example be a 1 ml syringe 3.

The auto-injector 1 is always needle-safe as the needle 4 can be retracted before the delivery of the medicament M is complete.

As only the plunger 10 is subjected to the relatively high force of the drive spring 9, the other components of the auto-injector 1 are not affected, so reliability and shelf life are increased.

The auto-injector 1 is suited to be used as a platform as the drive spring 9 can be swapped to deliver different viscosity drugs without affecting the insertion or retraction functions. This is particularly advantageous for high-viscosity fluids.

The plunger release mechanisms 12, 120 may be applied in a drug delivery device 1, e.g. an auto-injector 1, without the described feedback mechanism 13, first and second shroud lock mechanism 15, 16 and needle sheath removal mechanism 17 or with other types of one or more of these mechanisms.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days).

In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 auto-injector, drug delivery device
1.1 control subassembly
1.2 drive subassembly
2 case
2.1 front case
2.2 rear case
2.3 longitudinal slot
2.6 proximal end
2.9 distal arm
2.10 case rib
2.11 ramped surface
2.12 stop
2.13 angular stop
2.15 radial stop
3 syringe, medicament container
4 needle
5 protective needle sheath
6 stopper
7 needle shroud
7.3 shroud boss 7.4 shroud beam
7.6 aperture
8 control spring
9 drive spring
10 plunger
10.1 plunger boss
11 cap
11.3 compliant beam
11.4 rib
11.5 grip feature
11.7 sheath removal beam
11.8 inward ledge
11.10 distal face
11.11 opening
11.12 rib
12 plunger release mechanism
13 feedback mechanism
14 collar
14.1 cam surface
14.2 first collar rib
14.3 second collar rib
14.4 third collar rib
14.5 inner protrusion
14.6 snap-fit joint
14.10 interface
14.11 first longitudinal surface
14.12 transversal surface
14.13 second longitudinal surface
14.14 lateral surface
14.15 lateral surface
14.16 distal surface
15 first shroud lock mechanism
16 second shroud lock mechanism
17 needle sheath removal mechanism
18 carrier
120 plunger release mechanism
D distal direction
M medicament
P proximal direction
P1 proximal position
P2 distal position
R1 first rotational direction
R2 second rotational direction
S1 distal position
S2 proximal position

The invention claimed is:

1. A drug delivery device comprising:
a case configured to retain a medicament container;
a plunger disposed within the case and slidable from a proximal position into a distal position for delivering a medicament from the medicament container;
a drive spring disposed within the case and configured to provide energy in order to move the plunger from the proximal position into the distal position; and
a feedback mechanism operatively connected with the plunger, the feedback mechanism comprising:
a collar,
a needle shroud, and
a control spring separate from the drive spring, and configured to bias the needle shroud in a distal direction relative to the collar,
wherein the collar is operatively coupled to the case in an axial direction and prevented from axially decoupling from the case by the plunger when in the proximal position,
wherein the plunger, during movement from the proximal position towards the distal position, is configured to allow axial decoupling of the collar from the case so that the collar, driven by the control spring, moves in a proximal direction, opposite the distal direction, until movement of the collar in the proximal direction is halted to create an audible feedback, a tactile feedback, or the audible and tactile feedback.

2. The drug delivery device according to claim 1, wherein the collar is adapted to abut the case to create the audible feedback, the tactile feedback, or the audible and tactile feedback.

3. The drug delivery device according to claim 1, wherein the collar comprises one or more resilient joints adapted to axially interact with the case, the joints biased inward, wherein the plunger in the proximal position is adapted to inwardly support the joints to prevent their inward movement and wherein the plunger in the distal position is axially removed from the joints, allowing their inward movement and allowing decoupling of the joints from the case.

4. The drug delivery device according to claim 1, comprising a plunger release mechanism adapted to prevent release of the plunger when the needle shroud is in a distal position and adapted to release the plunger when the needle shroud is in a proximal position.

5. The drug delivery device according to claim 4, wherein the plunger release mechanism comprises a cam surface on the collar and a plunger boss configured to engage the cam surface such that a distally-directed force applied to the plunger causes the plunger boss to abut the cam surface to bias the collar in a rotational direction.

6. The drug delivery device according to claim 5, wherein the plunger boss is guided in a longitudinal slot within the case.

7. The drug delivery device according to claim 6, wherein the slot is wider than the plunger boss, allowing rotational movement of the plunger boss and the plunger relative to the case.

8. The drug delivery device according to claim 4, comprising a shroud boss arranged on the needle shroud and adapted to contact a first collar rib on the collar during assembly of the drug delivery device, and wherein one or both of the shroud boss and the first collar rib are angled such that proximal motion of the needle shroud causes the collar to rotate.

9. The drug delivery device according to claim 8, wherein the plunger release mechanism comprises a cam surface on the collar and a plunger boss configured to engage the cam surface such that a distally-directed force applied to the plunger causes the plunger boss to abut the cam surface to bias the collar in a rotational direction, wherein the cam surface comprises two ramps defining a tip, wherein the rotation of the collar due to the proximal motion of the needle shroud during assembly of the drug delivery device causes the plunger boss to move past the tip of the cam surface.

10. The drug delivery device according to claim 8, wherein the plunger release mechanism comprises a cam surface on the collar and a plunger boss configured to engage the cam surface such that a distally-directed force applied to the plunger causes the plunger boss to abut the cam surface to bias the collar in a rotational direction, comprising an L-shaped second collar rib on the collar, configured to laterally abut the shroud boss to prevent further rotation of the collar and to maintain a coupling of the cam surface to the plunger boss when the needle shroud is in the distal position, and wherein the shroud boss disengages the second collar rib when the needle shroud is in the proximal position, such that further rotation of the collar to decouple the plunger boss from the cam surface to release the plunger is allowed.

11. The drug delivery device according to claim 4, comprising an interface on the collar adapted to engage a case rib on the case, and wherein the interface comprises two lateral surfaces adapted to operatively abut the case rib, such that rotation of the collar relative to the case is allowed.

12. The drug delivery device according to claim 11, wherein the interface comprises a distal surface adapted to abut the case rib to prevent movement of the collar in the distal direction relative to the case.

13. The drug delivery device according to claim 10, comprising a ramped surface adapted to abut the collar as the collar moves after release of the feedback mechanism, the abutment of the ramped surface imparting a torque on the collar for aligning the second collar rib in an axial path of the shroud boss after extension of the needle shroud from the proximal position to the distal position.

14. The drug delivery device according to claim 13, comprising an angular stop adapted to abut the collar and prevent rotation of the collar beyond alignment of the second collar rib in the axial path of the shroud boss.

15. A drug delivery device comprising:
a case configured to retain a medicament container;
a plunger disposed within the case and slidable from a proximal position into a distal position for delivering a medicament from the medicament container;
a feedback mechanism operatively connected with the plunger, the feedback mechanism comprising:
a collar,
a needle shroud, and
a control spring configured to bias the needle shroud in a distal direction relative to the collar,
wherein the collar is operatively coupled to the case in an axial direction and prevented from axially decoupling from the case by the plunger when in the proximal position, wherein the plunger, during movement from the proximal position towards the distal position, is configured to allow axial decoupling of the collar from the case driven by the control spring until movement of the collar is halted to create an audible and/or tactile feedback; and
a plunger release mechanism configured to prevent release of the plunger when the needle shroud is in a distal position and configured to release the plunger when the needle shroud is in a proximal position, the plunger release mechanism comprising:
a cam surface on the collar, and
a plunger boss configured to engage the cam surface such that a distally-directed force applied to the plunger causes the plunger boss to abut the cam surface to bias the collar in a rotational direction,
a shroud boss arranged on the needle shroud and configured to contact a first collar rib on the collar during assembly of the drug delivery device, wherein one or both of the shroud boss and the first collar rib are angled such that proximal motion of the needle shroud causes the collar to rotate; and
an L-shaped second collar rib on the collar, configured to laterally abut the shroud boss to prevent further rotation of the collar and to maintain coupling of the cam surface to the plunger boss when the needle shroud is in the distal position, and wherein the shroud boss disengages the second collar rib when the needle shroud is in the proximal position, such that further rotation of the collar to decouple the plunger boss from the cam surface to release the plunger is allowed.

16. The drug delivery device of claim 15, comprising the medicament container, wherein the medicament container contains the medicament, wherein the medicament is a pharmaceutically active compound.

17. The drug delivery device according to claim 1, wherein the case comprises a front case and a rear case adapted to be coupled to each other.

18. A drug delivery device comprising:
a case configured to retain a medicament container;
a plunger disposed within the case and slidable from a proximal position into a distal position for delivering a medicament from the medicament container;
a feedback mechanism operatively connected with the plunger, the feedback mechanism comprising:
a collar,
a needle shroud, and
a control spring configured to bias the needle shroud in a distal direction relative to the collar,
wherein the collar is operatively coupled to the case in an axial direction and prevented from axially decoupling from the case by the plunger when in the proximal position; and
a plunger release mechanism configured to prevent release of the plunger when the needle shroud is in a distal position and configured to release the plunger when the needle shroud is in a proximal position,
wherein the plunger, during movement from the proximal position towards the distal position, is configured to allow axial decoupling of the collar from the case driven by the control spring until movement of the collar in a proximal direction, opposite the distal direction, is halted to create an audible feedback, a tactile feedback, or the audible and tactile feedback,
wherein the plunger release mechanism comprises a cam surface on the collar and a plunger boss configured to engage the cam surface such that a distally-directed force applied to the plunger causes the plunger boss to abut the cam surface to bias the collar in a rotational direction.

* * * * *

UNITED STATES PATENT AND TRADEMARK OFFICE
CERTIFICATE OF CORRECTION

| | |
|---|---|
| PATENT NO. | : 11,160,927 B2 |
| APPLICATION NO. | : 15/578854 |
| DATED | : November 2, 2021 |
| INVENTOR(S) | : Thomas Mark Kemp and Hugo Revellat |

It is certified that error appears in the above-identified patent and that said Letters Patent is hereby corrected as shown below:

In the Specification

In Column 1, Line 9 (approx.), after "filed" delete "in"

Signed and Sealed this
Twenty-fifth Day of April, 2023

Katherine Kelly Vidal
*Director of the United States Patent and Trademark Office*